US010105547B2

(12) United States Patent
Gustavson et al.

(10) Patent No.: US 10,105,547 B2
(45) Date of Patent: Oct. 23, 2018

(54) WEARABLE CARDIOVERTER DEFIBRILLATOR (WCD) CAUSING PATIENT'S QRS WIDTH TO BE PLOTTED AGAINST THE HEART RATE

(71) Applicant: West Affum Holdings Corp., Grand Cayman (KY)

(72) Inventors: Laura M. Gustavson, Redmond, WA (US); David P. Finch, Bothell, WA (US); Joseph L. Sullivan, Kirkland, WA (US)

( * ) Notice: Subject to any disclaimer, the term of this patent is extended or adjusted under 35 U.S.C. 154(b) by 0 days.

(21) Appl. No.: 15/341,978

(22) Filed: Nov. 2, 2016

(65) Prior Publication Data

US 2017/0128735 A1    May 11, 2017

Related U.S. Application Data

(60) Provisional application No. 62/249,785, filed on Nov. 2, 2015.

(51) Int. Cl.
*A61B 5/00* (2006.01)
*A61N 1/39* (2006.01)
(Continued)

(52) U.S. Cl.
CPC ............ *A61N 1/3925* (2013.01); *A61B 5/002* (2013.01); *A61B 5/0022* (2013.01);
(Continued)

(58) Field of Classification Search
CPC .. A61N 1/0484; A61N 1/3993; A61N 1/3904; A61B 5/0452; A61B 5/0472
See application file for complete search history.

(56) References Cited

U.S. PATENT DOCUMENTS 3,724,355 A    4/1973 Unger
4,583,524 A    4/1986 Hutchins
(Continued)

FOREIGN PATENT DOCUMENTS

WO    1998039061 A2    9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Scott Getzow

(57) ABSTRACT

A wearable cardioverter defibrillator (WCD) system includes a support structure that the patient may wear, and one or more sensors that may acquire patient physiological signals, such as ECG and others. A processor of the WCD system may determine diagnostics from the patient physiological signals. These diagnostics include a six-second ECG portion, heart rates as histograms, heart rates against QRS width, heart rate trends, clinical event counters, diagnostics relating to heart rate variability and about the atrial arrhythmia burden of the patient. In some embodiments, the WCD system includes a user interface with a screen that displays these diagnostics. In some embodiments, the WCD system exports these diagnostics for viewing by a different screen. When viewed, these diagnostics permit more detailed analysis of the state of the patient.

30 Claims, 19 Drawing Sheets

*SAMPLE COMPONENTS OF EXTERNAL DEFIBRILLATOR*

(51) Int. Cl.
*A61N 1/04* (2006.01)
*A61B 5/024* (2006.01)
*A61B 5/04* (2006.01)
*A61B 5/046* (2006.01)
*A61B 5/0464* (2006.01)
*A61B 5/0472* (2006.01)
*A61B 5/0205* (2006.01)
*A61B 5/0456* (2006.01)

(52) U.S. Cl.
CPC .......... *A61B 5/02405* (2013.01); *A61B 5/046* (2013.01); *A61B 5/04012* (2013.01); *A61B 5/0464* (2013.01); *A61B 5/0472* (2013.01); *A61B 5/6805* (2013.01); *A61B 5/6831* (2013.01); *A61B 5/7445* (2013.01); *A61B 5/7475* (2013.01); *A61N 1/046* (2013.01); *A61N 1/0484* (2013.01); *A61N 1/3904* (2017.08); *A61N 1/3968* (2013.01); *A61N 1/3993* (2013.01); *A61B 5/0205* (2013.01); *A61B 5/0456* (2013.01); *A61B 5/7275* (2013.01); *A61B 5/746* (2013.01); *A61B 2505/01* (2013.01); *A61B 2505/07* (2013.01)

(56) References Cited

U.S. PATENT DOCUMENTS

| | | | |
|---|---|---|---|
| 4,619,265 | A | 10/1986 | Morgan et al. |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,353,793 | A | 10/1994 | Bornn |
| RE34,800 | E | 11/1994 | Hutchins |
| 5,394,892 | A | 3/1995 | Kenny |
| 5,405,362 | A | 4/1995 | Kramer et al. |
| 5,474,574 | A | 12/1995 | Payne et al. |
| 5,662,690 | A | 9/1997 | Cole et al. |
| 5,782,878 | A | 7/1998 | Morgan et al. |
| 5,792,204 | A | 8/1998 | Snell |
| 5,902,249 | A | 5/1999 | Lyster |
| 5,913,685 | A | 6/1999 | Hutchins |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,263,238 | B1 | 7/2001 | Brewer et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder |
| 6,437,083 | B1 | 7/2002 | Owen et al. |
| 6,529,875 | B1 | 3/2003 | Nakajima |
| 6,546,285 | B1 | 4/2003 | Owen et al. |
| 6,681,003 | B2 | 1/2004 | Linder et al. |
| 6,762,917 | B1 | 7/2004 | Verbiest et al. |
| 7,065,401 | B2 | 6/2006 | Worden |
| 7,559,902 | B2 | 7/2009 | Ting et al. |
| 7,865,238 | B2 | 1/2011 | Brink |
| 7,870,761 | B2 | 1/2011 | Valentine et al. |
| 7,974,689 | B2 | 7/2011 | Volpe et al. |
| 8,140,154 | B2 | 10/2012 | Donnelly et al. |
| 8,369,944 | B2 | 2/2013 | Macho et al. |
| 8,644,925 | B2 | 2/2014 | Volpe et al. |
| 8,965,500 | B2 | 2/2015 | Macho et al. |
| 9,008,801 | B2 | 4/2015 | Kaib et al. |
| 9,131,901 | B2 | 9/2015 | Volpe et al. |
| 9,132,267 | B2 | 9/2015 | Kaib |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2008/0312709 | A1 | 12/2008 | Volpe et al. |
| 2009/0005827 | A1 | 1/2009 | Weintraub et al. |
| 2010/0007413 | A1 | 1/2010 | Herleikson |
| 2010/0298899 | A1 | 11/2010 | Donnelly et al. |
| 2011/0022105 | A9* | 1/2011 | Owen .................. A61N 1/0452 607/5 |
| 2011/0251504 | A1* | 10/2011 | Tereshchenko .... A61B 5/04011 600/512 |
| 2011/0288604 | A1 | 11/2011 | Kaib et al. |
| 2011/0288605 | A1 | 11/2011 | Kaib et al. |
| 2011/0319777 | A1* | 12/2011 | Mehrotra .............. A61B 5/0006 600/509 |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0265265 | A1 | 10/2012 | Razavi et al. |
| 2012/0283794 | A1 | 11/2012 | Kaib et al. |
| 2012/0302860 | A1 | 11/2012 | Volpe et al. |
| 2013/0085538 | A1 | 4/2013 | Volpe et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0025131 | A1 | 1/2014 | Sullivan et al. |
| 2014/0070957 | A1 | 3/2014 | Longinotti-Buitoni et al. |
| 2014/0194762 | A1* | 7/2014 | Kuppuraj ............. A61B 5/0404 600/515 |
| 2014/0324112 | A1 | 10/2014 | Macho et al. |
| 2014/0378812 | A1 | 12/2014 | Saroka et al. |
| 2015/0039053 | A1 | 2/2015 | Kaib et al. |
| 2016/0004831 | A1 | 1/2016 | Carlson et al. |

OTHER PUBLICATIONS

Lifecor LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Heartstart MRx and XL AED Algorithm—Application Note, Jul. 2001, Edition 2 Philips Healthcare, USA.
The LifeVest Network/Patient Data Management System, Zoll, 2015, 20C0503 Rev A.
Irhythm, St. Jude Medical, ZIO Patch Report, 2011, pp. 1-16, San Francisco, CA USA.
Medtronic Cardiac Rhythm Management, Cardiac Compass Device Features, 2013, pp. 1-8, Minneapolis, MN, USA.
Zoll LifeVest, ECG Report, 2013, LifeVest Network, 2013, pp. 1-10, USA.
Zoll LifeVest, The LifeVest Network Patient Data Management System, 20C0503 Rev A, 2015, pp. 1-4, USA.

* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

COMPONENTS OF SAMPLE COMBINATION

FIG. 6 — WCD METHODS FOR SIX-SECOND ECG DISPLAY

FIG. 8 — WCD METHODS FOR HEART RATE HISTOGRAM DISPLAY

FIG. 10 — WCD METHODS FOR QRSW V. HEART RATE DISPLAY

FIG. 12 — WCD METHODS FOR HEART RATE TRENDS DISPLAY

FIG. 14 — WCD METHODS FOR CLINICAL COUNTERS DISPLAY

FIG. 16 — WCD METHODS FOR HEART RATE VARIABILITY DISPLAY

WEARABLE CARDIOVERTER DEFIBRILLATOR (WCD) CAUSING PATIENT'S QRS WIDTH TO BE PLOTTED AGAINST THE HEART RATE

CROSS REFERENCE TO RELATED PATENT APPLICATIONS

This patent application claims priority from U.S. Provisional Patent Application Ser. No. 62/249,785, filed on Nov. 2, 2015, the disclosure of which, as initially made, is hereby incorporated by reference.

BACKGROUND

When people suffer from some types of heart arrhythmias, the result may be that blood flow to various parts of the body is reduced. Some arrhythmias may even result in a sudden cardiac arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an implantable cardioverter defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a wearable cardioverter defibrillator (WCD) system. (Early versions of such systems were called wearable cardiac defibrillator (WCD) systems) A WCD system typically includes a harness, vest, or other garment that the patient is to wear. The WCD system includes a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart, to restore proper sinus rhythm.

BRIEF SUMMARY

The present description gives instances of a wearable cardioverter defibrillator (WCD) systems, storage media that store programs, and methods, the use of which may help overcome problems and limitations of the prior art.

In embodiments, a wearable cardioverter defibrillator (WCD) system includes a support structure that the patient may wear, and one or more sensors that may acquire patient physiological signals, such as ECG and others. A processor of the WCD system may determine diagnostics from the patient physiological signals. These diagnostics include a six-second ECG portion, heart rates as histograms, heart rates against QRS width, heart rate trends, clinical event counters, diagnostics relating to heart rate variability and about the atrial arrhythmia burden of the patient. In some embodiments, the WCD system includes a user interface with a screen that displays these diagnostics. In some embodiments, the WCD system exports these diagnostics for viewing by a different screen. When viewed, these diagnostics permit more detailed analysis of the state of the patient.

These and other features and advantages of the claimed invention will become more readily apparent in view of the embodiments described and illustrated in the present disclosure, namely from the present written specification and the drawings.

DETAILED DESCRIPTION

As has been mentioned, the present description is about wearable cardioverter defibrillator (WCD) devices, systems, storage media that store programs, and methods. Embodiments are now described in more detail.

A wearable cardioverter defibrillator (WCD) system made according to embodiments has a number of components. These components can be provided separately as modules that can be interconnected, or can be combined with other components, etc.

A component of a WCD system can be a support structure, which is configured to be worn by the patient. The support structure can be any structure suitable for wearing, such as a harness, a vest, a half-vest—for example over the left side of the torso that positions electrodes on opposite sides of the heart, one or more belts that are configured to be worn horizontally or possibly vertically over a shoulder, another garment, and so on. The support structure can be implemented in a single component or multiple components. For example, a support structure may have a top component resting on the shoulders, for ensuring that the defibrillation electrodes will be in the appropriate positions for defibrillating, and a bottom component resting on the hips, for carrying the bulk of the weight of the defibrillator. A single component embodiment could be with a belt around at least the torso. Other embodiments could use an adhesive structure or another way for attaching to the patient, without encircling any part of the body. There can be other examples.

Figure 1:
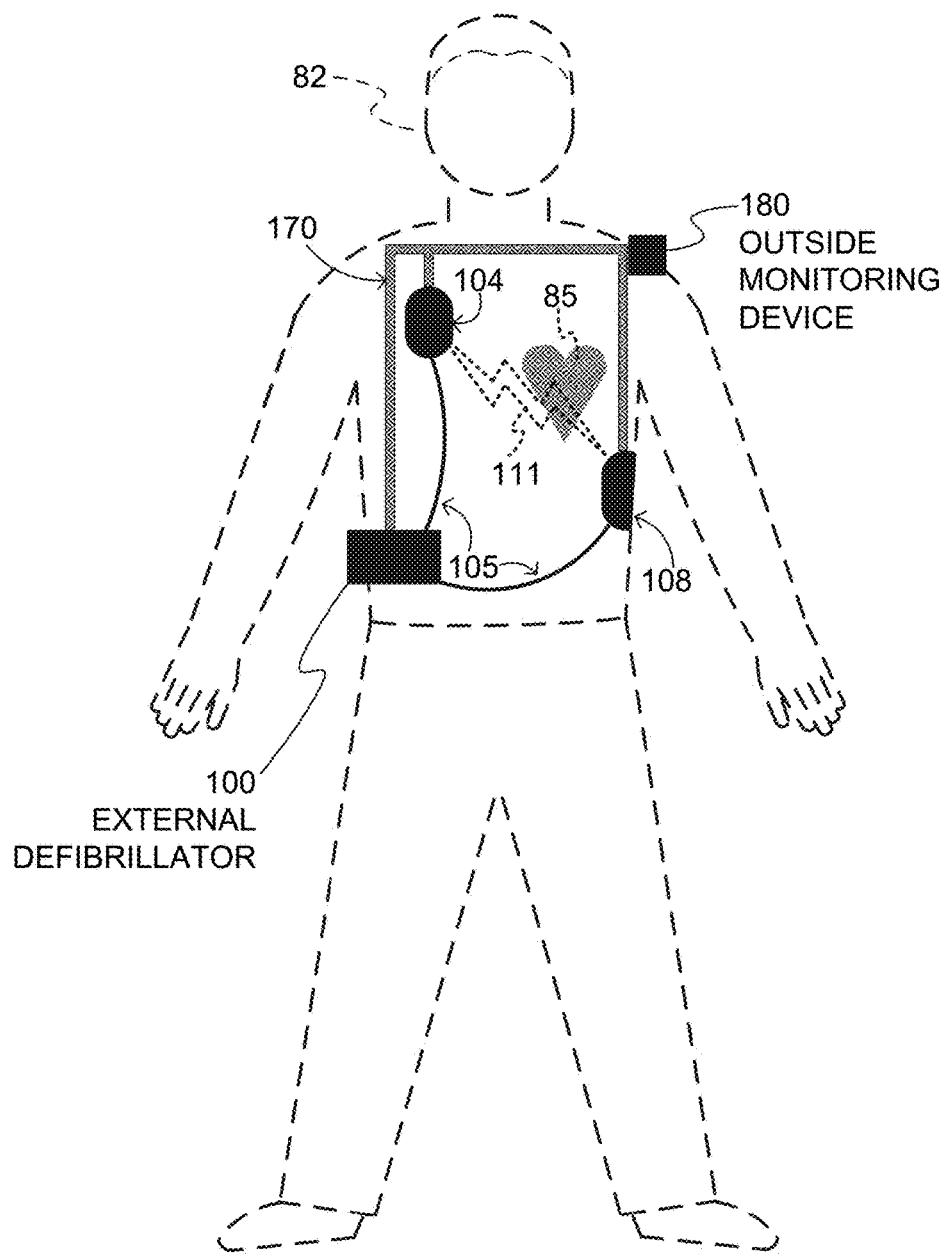
FIG. 1 is a diagram of components of a sample wearable cardioverter defibrillator (WCD) system, made according to embodiments.

FIG. 1 depicts components of a WCD system made according to embodiments, as it might be worn by a patient 82. A patient such as patient 82 may also be referred to as a person and/or wearer, since that patient wears components of the WCD system.

In FIG. 1, a generic support structure 170 is shown relative to the body of patient 82, and thus also relative to his or her heart 85. Structure 170 could be a harness, a vest, a half-vest, one or more belts, or a garment, etc., as per the above. Structure 170 could be implemented in a single component, or multiple components, and so on. Structure 170 is wearable by patient 82, but the manner of wearing it is not depicted, as structure 170 is depicted only generically in FIG. 1 and, in fact, partly conceptually. That is, FIG. 1 is provided merely to illustrate concepts about the support structure 170 and is not to be construed as limiting it.

A WCD system according to embodiments is configured to defibrillate a patient who is wearing it, by delivering an electric charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as a defibrillation shock or therapy shock, is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, defibrillator 100 may initiate defibrillation (or hold-off defibrillation) based on a variety of inputs, with the ECG being merely one of them.

Accordingly, it will be appreciated that signals such as physiological signals containing physiological data are obtained from patient 82. While the patient may be a considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter, in other words be or act as a sensor. A local parameter can be a parameter of patient 82, or a parameter of the WCD system, or a parameter of the environment, as will be described later in this document. Device 180 may include one or more transducers that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
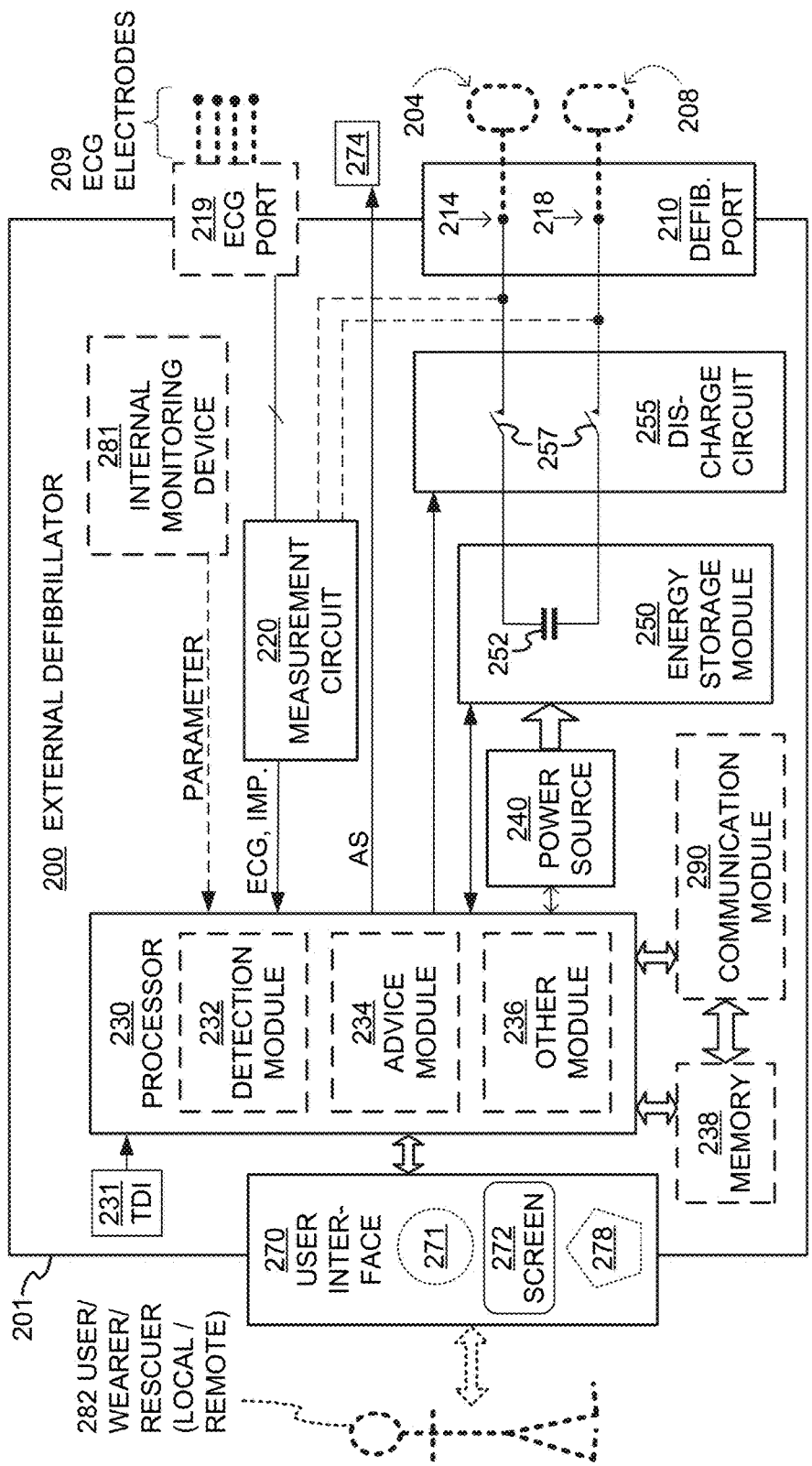
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 270 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 270 can be made in any number of ways. User interface 270 may include output devices, which can be visual, audible or tactile, for communicating to a user. For example, an output device can be a light, or a screen 272 to display what is sensed, detected and/or measured or computed, and provide visual feedback to rescuer 282 for their resuscitation attempts, and so on. Another output device can be a speaker, which can be configured to issue voice prompts, etc. Sounds, images, vibrations, and anything that can be perceived by user 282 can also be called human perceptible indications.

User interface 270 may also include input devices for receiving inputs from users. A sample input device 278 is shown. In some embodiments, user inputs are received remotely, e.g. from input device 379 via link 304, as is also described in FIG. 3. Returning to FIG. 2, the user inputs can be received by processor 230, and in turn control the WCD system, provide information to it and so on. Such input devices may by implemented by various controls, such as pushbuttons, keyboards, actuators, touchscreens, a microphone, and so on. Such input devices can be configured to receive a user input from person 282, who can be the wearer, a rescuer, etc. For example, an input device can be a trigger 271, which is sometimes called a cancel switch, or a "live-man" switch, or "I am alive" switch. In some embodiments, the rescuer actuating trigger 271 can prevent the impending delivery of a shock; by actuating the trigger, the wearer can prevent the discharge of the electric charge.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1, be or act as a sensor, etc. Allocating which of the system parameters are to be monitored by which monitoring device can be done according to design considerations. Device 281 may include one or more transducers that are configured to render one or more physiological inputs from one or more patient parameters that it senses. Of course, device 281 is provided above and beyond ECG port 219.

Patient physiological parameters include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device may include one or more sensors configured to acquire patient physiological signals. Examples of such sensors include electrodes to detect ECG data, a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an $SpO_2$ sensor, and so on. It will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 82. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 82 will know about a condition that is either not improving or deteriorating.

Patient state parameters include recorded aspects of patient 82, such as motion, posture, whether they have spoken recently plus maybe also what they said, and so on, plus optionally the history of these parameters. Or, one of these monitoring devices could include a location sensor such as a global positioning system (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, the transducer includes a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. A humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. In some embodiments, defibrillation electrodes 204, 208 are instead connected continuously to defibrillation port 210. Either way, defibrillation port 210 can be used for guiding, via these electrodes, to the wearer the electric charge that has been stored in energy storage module 250. The electric charge can be be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a WCD system according to embodiments also includes a fluid that it can deploy automatically between the electrodes and the patient skin. The fluid can be conductive, such as by including an electrolyte, for making a better electrical contact between the electrode and the skin. Electrically speaking, when the fluid is deployed, the electrical impedance between the electrode and the skin is reduced.

Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir (not shown in FIG. 2), which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated responsive to receiving activation signal AS from processor 230, prior to the electrical discharge.

In some embodiments, defibrillator 200 also includes a transducer that includes a measurement circuit 220. Measurement circuit 220 senses one or more electrical physiological signal of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from measurement circuit 220. However, an output of measurement circuit 220 can be called an input when received as an input by a subsequent device or functionality.

Defibrillator 200 also includes a temporal data input (TDI) 231. TDI 231 may be implemented by a clock or analogous structure. TDI 231 can be configured to provide time stamps indicating respective times of acquisition for patient physiological signals acquired by other devices or functionalities of a WCD system made according to embodiments.

Defibrillator 200 also includes a processor 230. Processor 230 may be implemented in a number of ways. Such ways include, by way of example and not of limitation, digital and/or analog processors such as microprocessors and digital signal processors (DSPs); controllers such as microcontrollers; software running in a machine; programmable circuits such as field programmable gate arrays (FPGAs), field-programmable analog arrays (FPAAs), programmable logic devices (PLDs), application specific integrated circuits (ASICs), any combination of one or more of these, and so on. TDI 231 may be implemented as a stand-alone functionality, or as part of processor 230.

The processor 230 may include, or have access to, non-volatile memory for storage of machine readable and machine executable instructions. The instructions, which may also referred to as software, generally provide for functionality by performing methods as may be disclosed herein or understood by one skilled in the art in view of the disclosed embodiments. In some embodiments, and as a matter of convention used herein, instances of the software may be referred to as a "module" and by other similar terms. Generally, where introduced as a module, the instruction set is provided to offer or fulfill a particular functionality. Embodiments of modules and the functionality delivered are not limited by the embodiments set forth herein.

Processor 230 can be considered to have a number of modules. One such module can be a detection module 232. Detection module 232 can include a ventricular fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a ventricular tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more of ECG signals that are captured according to embodiments, and determining whether a shock criterion is met. The determination can be made from a rhythm analysis of the captured ECG signal or otherwise.

In some embodiments, when the determination is to shock, an electric charge is delivered to the patient. Delivering the electric charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, nonvolatile memories (NVM), read-only memories (ROM), random access memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, processes, operations, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. The data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 additionally includes an energy storage module 250, which can thus be coupled to the support structure of the WCD system. Module 250 is where some electrical energy can be stored temporarily in the form of an electric charge, when preparing it for discharge to administer a shock. In embodiments, module 250 can be charged from power source 240 to the right amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electric charge, for delivering to the patient.

Defibrillator 200 moreover includes a discharge circuit 255. When the decision is to shock, processor 230 can be configured to control discharge circuit 255 to discharge through the patient the electric charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 270.

Defibrillator 200 can optionally include a communication module 290, for establishing one or more wired or wireless communication links with other devices of other entities, such as a remote assistance center, Emergency Medical Services (EMS), and so on. Module 290 may also include an antenna, portions of a processor, and other sub-components as may be deemed necessary by a person skilled in the art. This way, data and commands can be communicated, such as patient data, event information, therapy attempted, CPR performance, system data, environmental data, and so on.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

In some embodiments, one or more of the sensors in this description are configured to acquire patient physiological signals, which can be different signals in different embodiments. In addition, TDI 231 can optionally be configured to provide time stamps indicating respective times of acquisition of the patient physiological signals that are acquired by the one or more sensors. These time stamps can be either express times, incremented marks as to a reference time, and so on. Moreover, TDI 231 can optionally be configured to provide time stamps indicating respective times of acquisition of patient steps, times when events occurred such as those for clinical counters, the trigger being actuated, and so on.

In some embodiments, memory 238 is configured to store values of the patient physiological signals. Optionally, memory 238 is further configured to store the time stamps that indicate the times of acquisition for the stored patient physiological signals. Or, the values can be stored successively, with the understanding that they are captured at known intervals, such as even intervals, and so on.

In embodiments, processor 230 is configured to compute, from the stored patient physiological signals, and the time stamps if also stored, various aspects of the patient physiological signals. Many examples of such aspects are described later in this document.

Moreover, screen 272 of user interface 270 can be configured to display the computed aspects, or just the acquired patient physiological signals. For example, processor 230 may cause screen 272 to so display, and so on. In fact, in some embodiments the screen can be configured to so display while the patient is wearing the support structure, and has been so wearing continuously since the patient physiological signals were acquired. Of course such results if stored can be also displayed later, in replay mode, etc.

It will be appreciated that the example of FIG. 2 is directed to embodiments that can be characterized as self-contained. Indeed, all operations, starting from the sensing and concluding with the displaying, may take place with embodiments carried by the patient. In such embodiments, the user interface can be configured to be coupled to the support structure. Moreover, the screen can be configured to display according to embodiments while the patient is wearing the support structure, and has been so wearing continuously since the patient physiological signals were acquired.

Other embodiments are now described, where the displaying is performed by a screen of another computer. Examples of such combination embodiments are now described.

Figure 3:
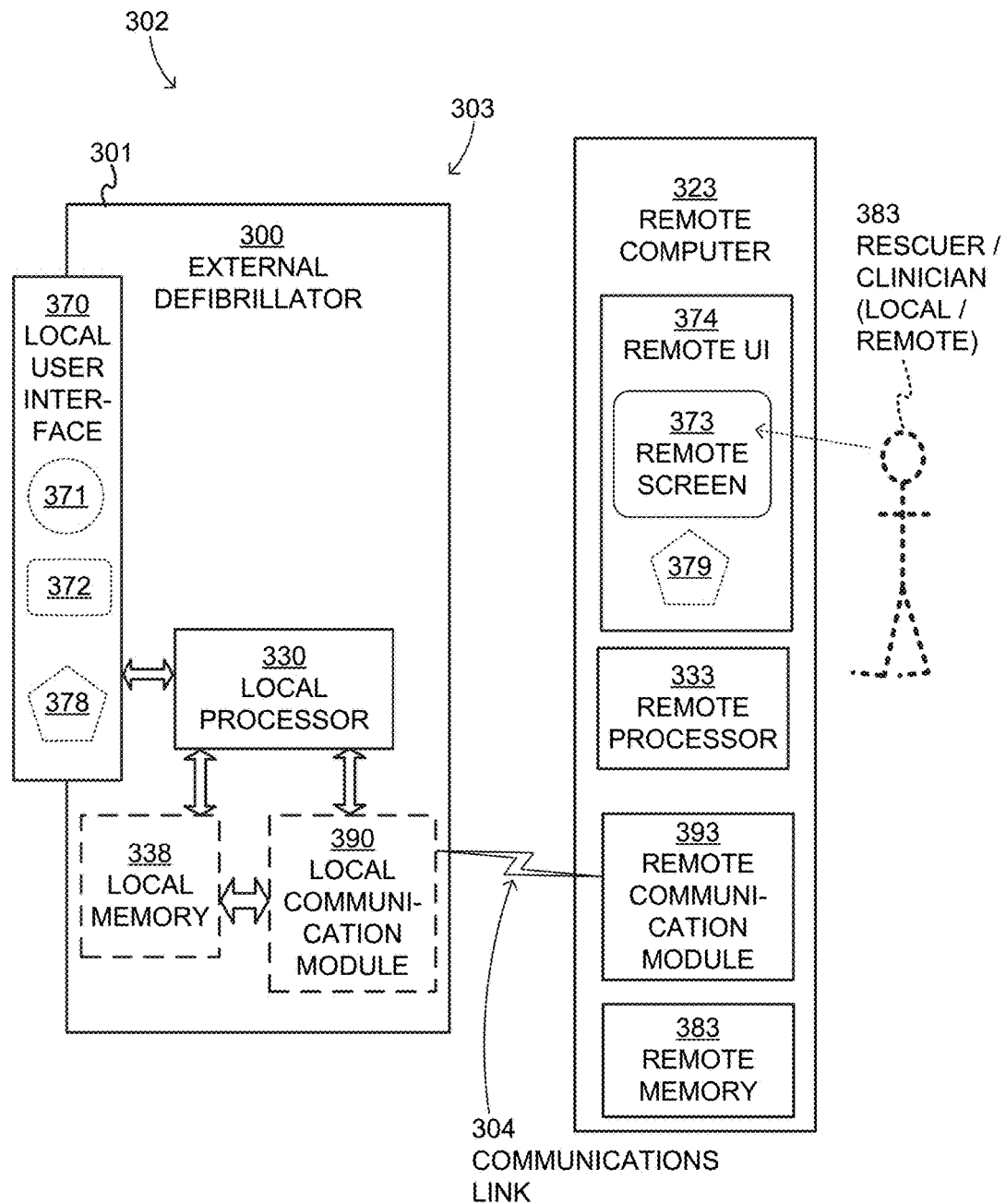
FIG. 3 is a diagram depicting some components of a sample combination according to embodiments.

Referring to FIG. 3, some components of a sample combination 302 are shown. Combination 302 includes a portion 303 of a WCD system, and a remote computer 323. Remote computer 323 is called "remote" only in the sense that it is not directly coupled to portion 303. In parallel, it will be recognized that a number of aspects of a WCD system according to a combination have been called "local".

Remote computer 323 can be used by a rescuer or clinician 383 who can be local or remote to the patient. Remote computer 323 may be a stationary computer at a rescuer station, or a mobile computer, such as a laptop computer, a tablet computer, a smartphone, and so on. In some embodiments, remote computer 323 can be a base station at the home of the patient, and is intended for use by the patient for a daily review and upload, instead of the rescuer.

In the example of FIG. 3, portion 303 includes an external defibrillator 300, which could be similar to, and have similar components as the above-described external defibrillator 200. Portion 303 may also include additional components, such as the ones previously described, but does not do so in order to not clutter FIG. 3. Such additional components of course may include the previously described support structure, power source, energy storage module discharge circuit, one or more sensors such as ECG electrodes, other electrodes, etc.

External defibrillator 300 may include, in a housing 301, a local processor 330, a local memory 338, a local communications module 390, and a local user interface 370 that includes a trigger 371, a local screen 372, and a local input device 378. Operations by local processor 330 can also be called local operations. All of these can be as described for similarly numbered components of FIG. 2, and can be further adapted for communicating using a communications link 304 as described below.

In the example of FIG. 3, remote computer 323 includes a remote communication module 393. Remote communication module 393 can be configured to receive data and commands from wireless communications link 304, as such may have been transmitted from local communication module 390. Communications link 304 may be over long or short distances, such as Bluetooth.

Remote computer 323 may also include a remote processor 333 and a remote memory 383. Operations by remote processor 333 can also be called remote operations. Remote computer 323 may be associated with a printer, from which to receive printouts. All views, graphs, etc. that a screen may display according to embodiments may also be received as printouts by a printer associated with remote computer 323, or with a WCD system, or another printer, etc.

Remote computer 323 may also include a remote user interface 374. Remote user interface 374 may include a remote input device 379, and a remote screen 373 that may be viewed by rescuer 383, as designated by an arrow. Remote input device 379 can be as described for input devices 278, 378, plus any other device available if remote computer 323 is implemented by a generic computer, portable or not.

In the example of FIG. 3, remote screen 373 can be configured to display any and all of the data, computed values and diagrams that are described in this document as possible to display on screen 272. Moreover, any and all data and values, sensed or computed by defibrillator 300, can be communicated via communications link 304, and stored in memory 383. Any of the processing described as possible for processor 330 may be performed by local processor 330, and may further or instead be performed by remote processor 333.

Going forward, while operations and possible displays may be described in terms of the embodiments of FIG. 2, that is only for simplicity. In fact, such operations and possible displays are also possible for combinations according to embodiments, such as combination 302, except where explicitly written so or construed otherwise.

In embodiments, the behavior or the patient's heart is detected. Frequently used patient physiological signals include the patient's electrocardiogram (ECG or EKG).

Figure 4:
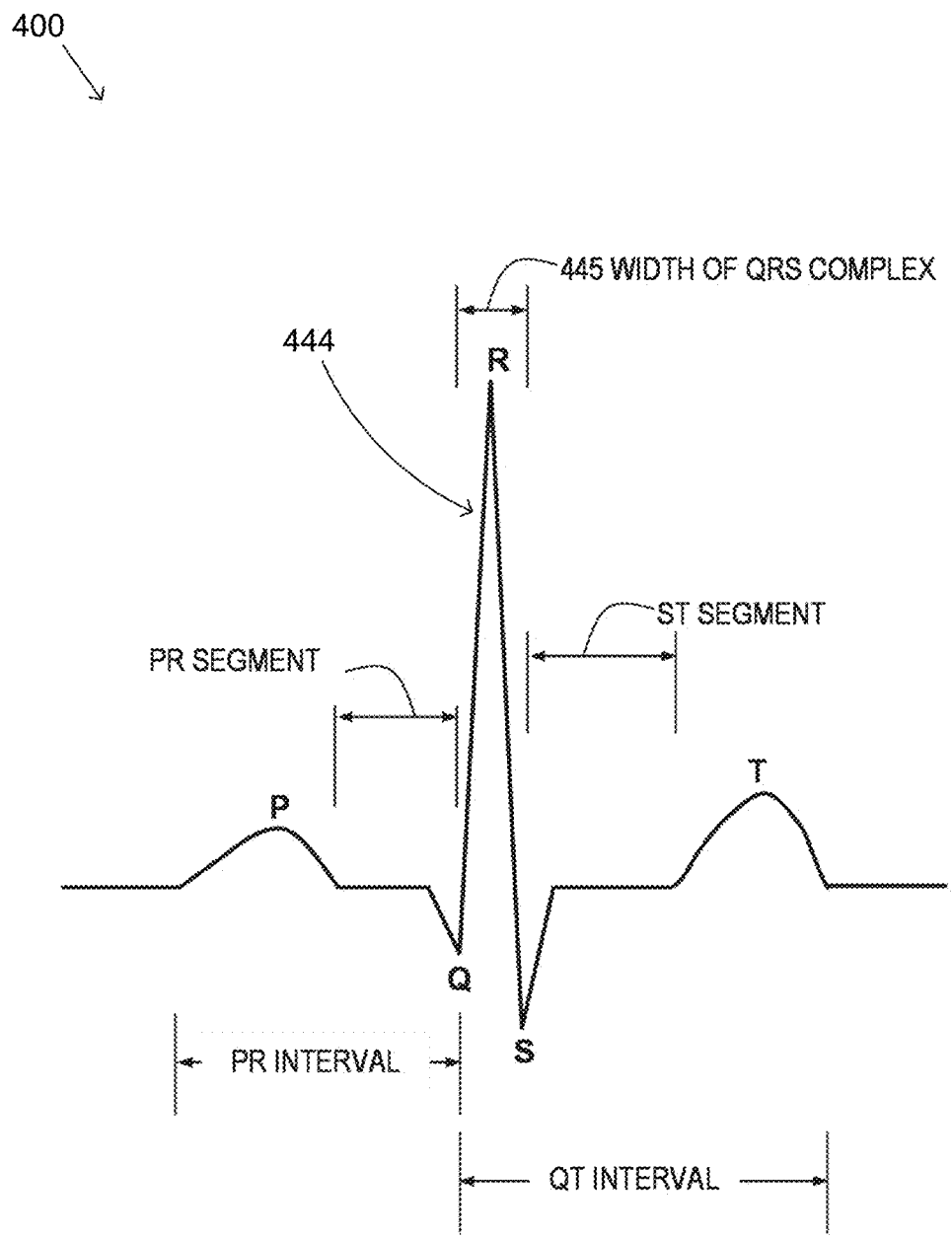
FIG. 4 is a graph depicting a single healthy heart pulse labeled according to clinical convention.

In FIG. 4, a known waveform portion 400 of a heart's ECG is rendered, along with various aspects of it. Of those aspects, a QRS complex 444 is a name for the combination of three of the graphical deflections (Q, R, S) seen on an ECG waveform. QRS complex 444 is usually the central and easiest part of the waveform to identify, as it appears like a spike. In this example, QRS complex 444 has a width designated by arrow 445. QRS complex 444 corresponds to the depolarization of the right and left ventricles of the human heart. The Q, R, and S waves occur in rapid succession, do not all appear in all leads, and reflect a single event, and thus are usually considered together. A Q wave is any downward deflection after the P wave. An R wave follows as an upward deflection, and the S wave is any downward deflection after the R wave. The T wave follows the S wave, and in some cases an additional U wave follows the T wave.

Returning to FIG. 2, in some embodiments, sensors such as ECG electrodes 209 or other electrodes 204, 208 may acquire ECG data of the patient. In such embodiments, screen 272 can be configured to display a diagram indicating a portion of the ECG data that lasts for six seconds. An example is now described.

Figure 5:
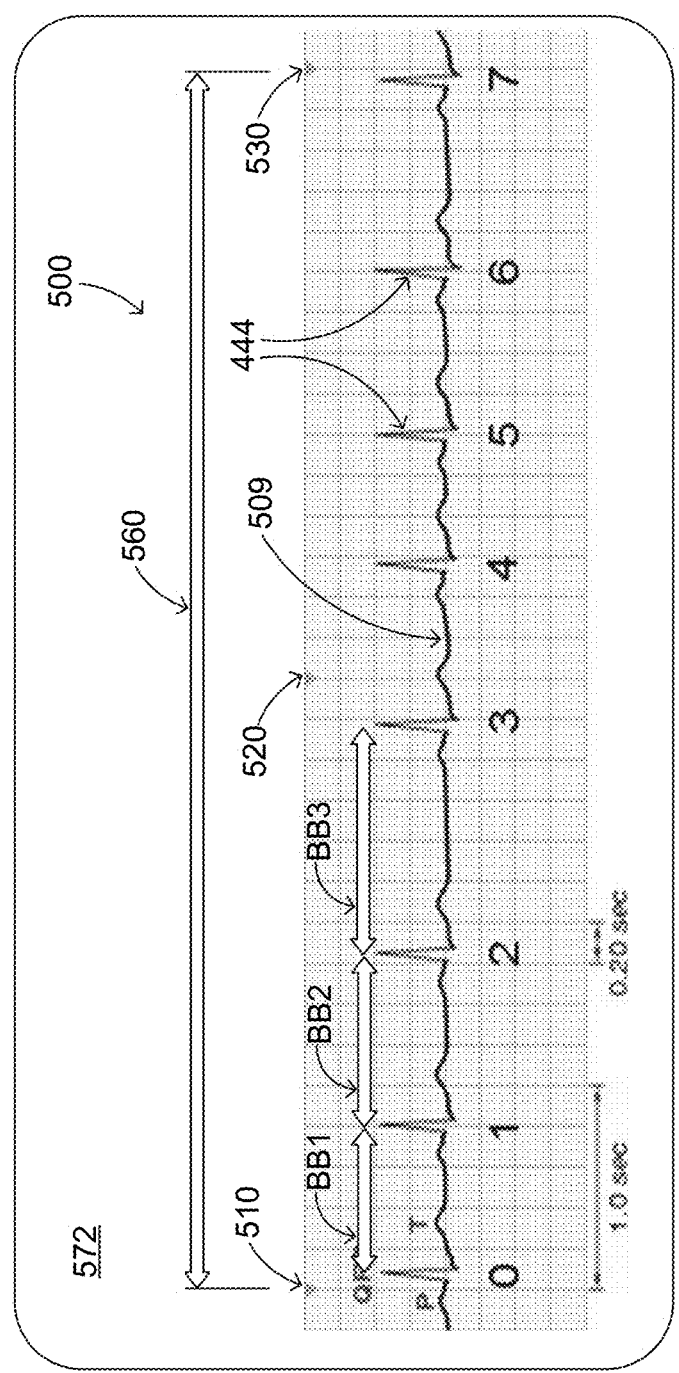
FIG. 5 is a diagram of a sample screen with a sample screenshot in embodiments where a six-second ECG portion is displayed.

FIG. 5 is a diagram of a sample screen 572 with a sample screenshot. Sample screen 572 could be, for example, any one of previously described screens 272, 372, 373. The screenshot of sample screen 572 is a diagram 500 of a six-second ECG display, in an embodiment where ECG data 509 is displayed along the horizontal direction, and appears as a waveform in an ECG rhythm strip. The horizontal direction is thus understood as a time axis, although no separate horizontal time axis need be explicitly provided for this and related embodiments.

To be more precise, screen 572 may graphically display a portion of the ECG data 509, which portion may last for somewhat longer than six seconds. In addition, diagram 500 may further demarcate a six-second portion of the displayed ECG data 509. In this example, the demarcating is implemented by further displaying indicators 510, 520, 530 in diagram 500. These indicators 510, 520, 530, taken in pairs are 3 sec apart. Accordingly, indicators 510 and 530 demarcate a duration of six seconds between them. This six-second duration is also shown as an arrow 560.

A feature visible from waveform 509 is the QRS complexes 444, which are described above. In addition, it is apparent that QRS complexes 444 do not occur at exactly regular intervals. Rather, beat-to-beat time intervals BB1, BB2, BB3 can be different from each other, in other words, having a variable duration.

The six-second depiction of FIG. 5 permits a quick, though approximate, calculation of the heart rate. Indeed, such a heart rate can be found by counting the number of QRS complexes 444 in data 509, and then multiplying that number by 10. In this example, there are 8 QRS complexes 444, numbered 0, 1, 2, ..., 7. The need to start with 0 and not 1 is because one is interested in really counting durations BB1, BB2, BB3, associated with QRS complexes 444. Accordingly, in this example the heart rate would be computed as approximately 7×10=70 bpm (beats per minute).

In some embodiments, data files are stored that encode, and can help recreate, successive views of the diagnostic graphs created according to embodiments. Such permits review by a clinician of the patient's history of diagnostic data. This review can be particularly helpful as to whether a change in patient care had an effect. Examples are now described.

Figure 19:
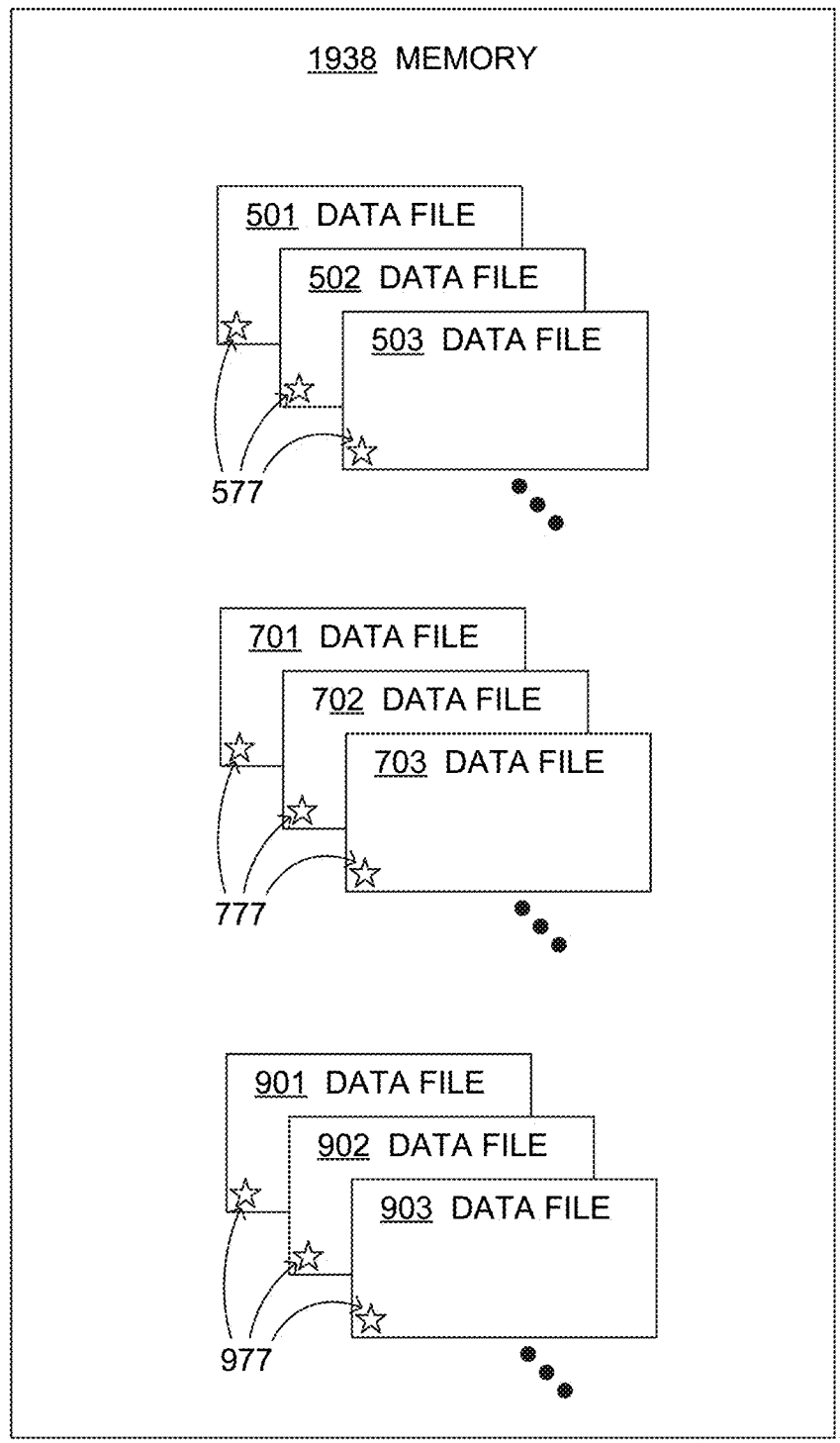
FIG. 19 is a block diagram illustrating possible contents of a memory according to embodiments.

FIG. 19 is a block diagram of a memory 1938, for discussing its possible contents according to embodiments. Memory 1938 can be memory 238, memory 338, memory 383, and so on. Memory 1938 can be configured to store data files that encode different displayed views according to embodiments, as snapshots. Encoding for the data files can be using the underlying values that generated the displayed diagram, an image of the diagram, and so on. In some of these embodiments, memory 1938 is further configured to store time stamps in association with the respective data files.

Data files may be stored in memory 1938 on different occasions. In some embodiments, storage is periodic; in other words an additional data file becomes thus stored after the passage of a preset aggregation time during which such diagnostic data is thus generated. If not set at a default value, the aggregation time may be set by the user, etc. Upon such storage, a fresh new data can start becoming aggregated, etc.

In other embodiments, storage can be commanded by the user; in other words, an additional data file can become thus stored responsive to receiving a user input from the input device. Again, upon such storage, a new file can be started, etc.

In the particular case of FIG. 5, different portions of the ECG data might be thus displayed on screens 272, 372, 373 as diagram 500 at different times. Moreover, a memory of a WCD system or of a combination according to embodiments, such as memory 1938, can be configured to store data files 501, 502, 503, . . . that encode the different portions as described. In some of these embodiments, memory 1938 can be further configured to store time stamps 577 in association with the respective data files 501, 502, 503, . . . .

The devices and/or systems mentioned in this document perform functions, operations, processes and/or methods. These functions, operations, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods according to embodiments are now described. These methods may also be performed by WCD systems made according to embodiments.

Figure 6:
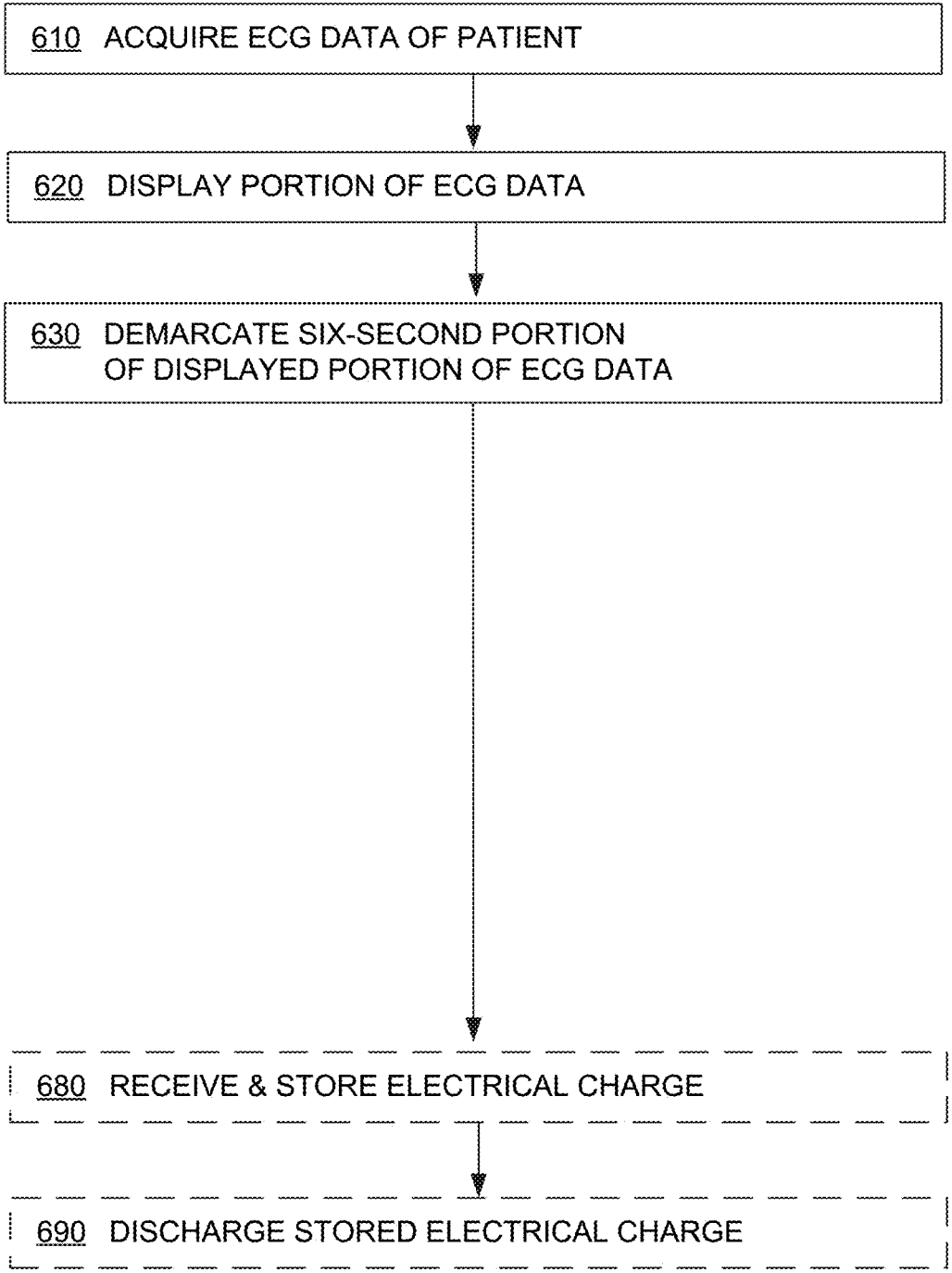
FIG. 6 is a flowchart for illustrating methods according to embodiments.

FIG. 6 shows a flowchart 600 for describing methods according to embodiments. According to an operation 610, electrocardiogram (ECG) data of the patient may be acquired, while the patient is wearing the support structure. Acquiring may be performed by one or more sensors, such as electrodes.

According to another operation 620, a portion of the ECG data may be displayed graphically on a screen.

According to another operation 630, a six-second portion of the displayed ECG data may be demarcated, for easy recognition. In embodiments, indicators, lines, or boundaries may be displayed so as to demarcate the six-second portion.

In addition, different portions of the ECG data may be thus displayed at different times. Data files can be stored in a memory, which encode the different portions. Plus, time stamps can be further stored in the memory in association with the respective data files. An additional data file may thus become thus stored after the passage of a preset aggregation time, or responsive to a user input being received from an input device.

According to another, optional operation 680, an electric charge may be received and stored in the energy storage module. The electric charge may be received from the power source.

According to another, optional operation 690, the stored electric charge may be discharged by the discharge circuit, while a support structure is worn by the patient.

In some embodiments, the WCD system itself computes one or more values for heart rates of the patient. Then the heart rates may be displayed in useful ways. In such embodiments the WCD system may include one or more sensors that are configured to acquire patient physiological signals. In such embodiments, a processor of the WCD system can be configured to determine, from the acquired patient physiological signals, heart rate values for heart rates of the patient. In particular, such signals can be, for example, ECG waveforms such as waveform 509, or pulse detection as described earlier in this document for various applicable sensors that can detect the pulse of the patient, and are configured to generate a signal responsive to such detection. It will be appreciated that some of these pulse sensors detect blood flow using mechanical pressure (e.g. NIBP), others using light ($SpO_2$), and so on. The processor may then discern or identify heart beats from the signals of these sensors. This discerning may be performed by performing mathematical recognition processes on ECG waveforms such as waveform 509, or on the other signals generated by these sensors, etc. Such recognition processes can be by comparing, filtering, etc. The processor may therefore determine, from the discerned heart beats, values for heart rates of the patient. The heart rate values may be yielded by sampling the heart rate periodically, for example once 1 minute, 10 minutes, 1 hour, 1 day, longer, etc.

Examples of displaying heart rates are now described. In some embodiments, a WCD system causes diagnostics about patient's heart rate to be displayed as a histogram.

The heart rate values may be determined over a time interval that will include an adequate number of samplings. Such a time interval can be of a suitable time duration, such as an hour, a day, a week, a month, and so on.

In some embodiments, these heart rate values may be displayed as a histogram by a screen of the user interface. Examples are now described.

Figure 7:
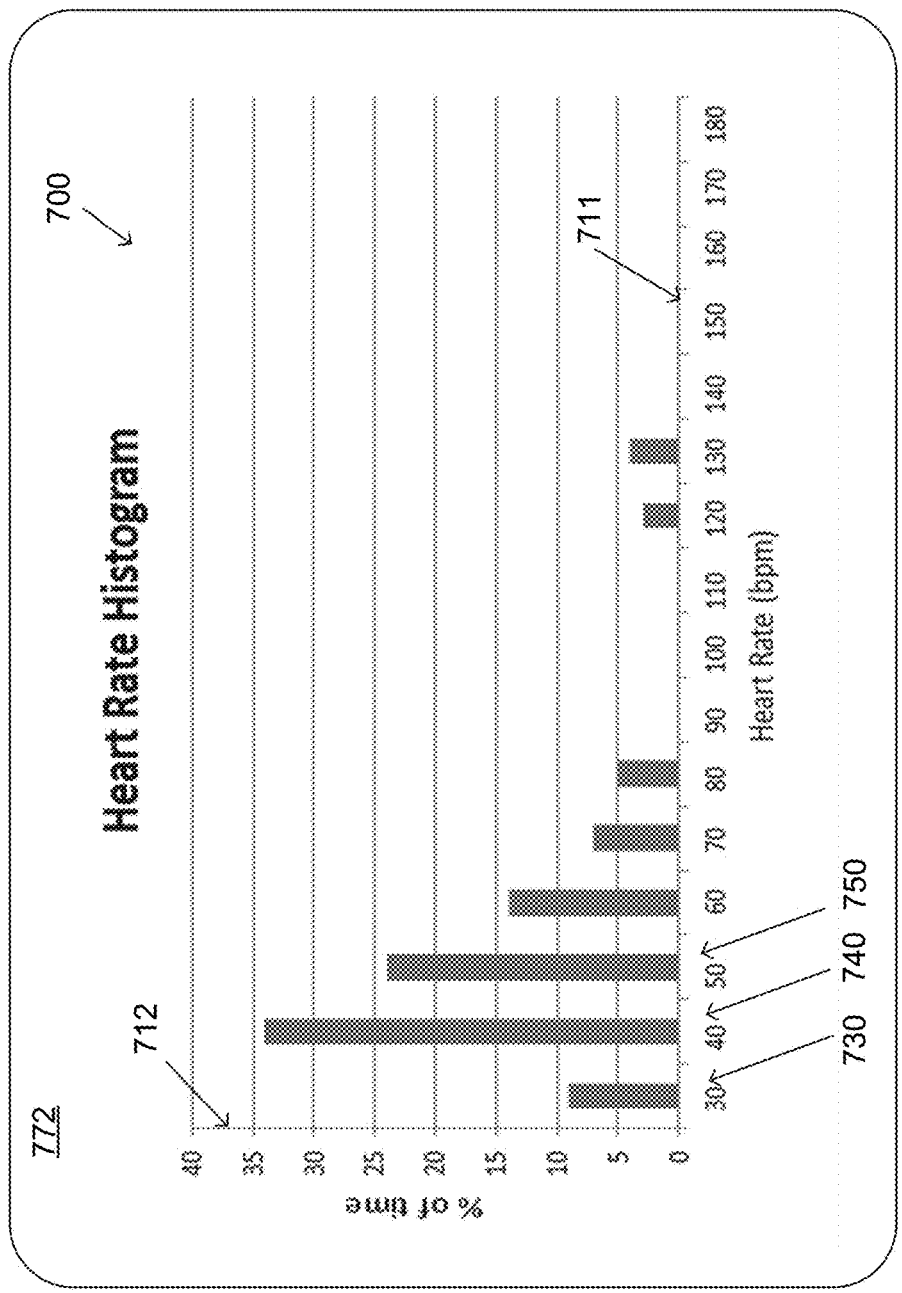
FIG. 7 is a diagram of a sample screen with a sample screenshot of distribution of heart rate values, shown as a histogram according to embodiments.

FIG. 7 is a diagram of a sample screen 772 with a sample screenshot. Sample screen 772 could be, for example, any one of previously described screens 272, 372, 373. The screenshot of sample screen 772 is a sample histogram 700 of heart rate values. In particular, ranges of possible heart rate values can be established. In the example of FIG. 7, the ranges are for every 10 bpm difference; sample ranges 730, 740, 750 are indicated with reference numerals.

In such embodiments, the processor may further classify at least some of the determined heart rate values as belonging in such respective ranges of possible heart rate values, each value in one range.

The processor may be able to further compute, for each one of the ranges, a respective count of how many of the determined heart rate values have been classified within that range. Moreover, the counts of the ranges can be totaled and normalized to 100. In the example of FIG. 7, range 730 has about 9% of the occurrences, range 740 about 34% of the occurrences, and so on.

It will be appreciated, then, that histogram 700 has indications of at least some of the ranges, arrayed along a horizontal time axis 711. These indications are together with the respective counts of at least some of the ranges, illustrated along a vertical axis 712. In this example, the illustration is by bars of heights that correspond to the respective counts.

This histogram representation has advantages. It provides the heart rate distribution over a monitoring period, and allows for the ability to reset counters, so as to establish a new baseline to monitor the effects of drug changes, for example.

In addition, previous versions of such histograms can be stored, for replay and review. More particularly, different versions of histogram 700 can be displayed on screens 272, 372, 373 at different times. Memory 1938 can be configured to store data files 701, 702, 703, . . . that encode the different versions of histogram 700, with respective time stamps 777, etc.

Figure 8:
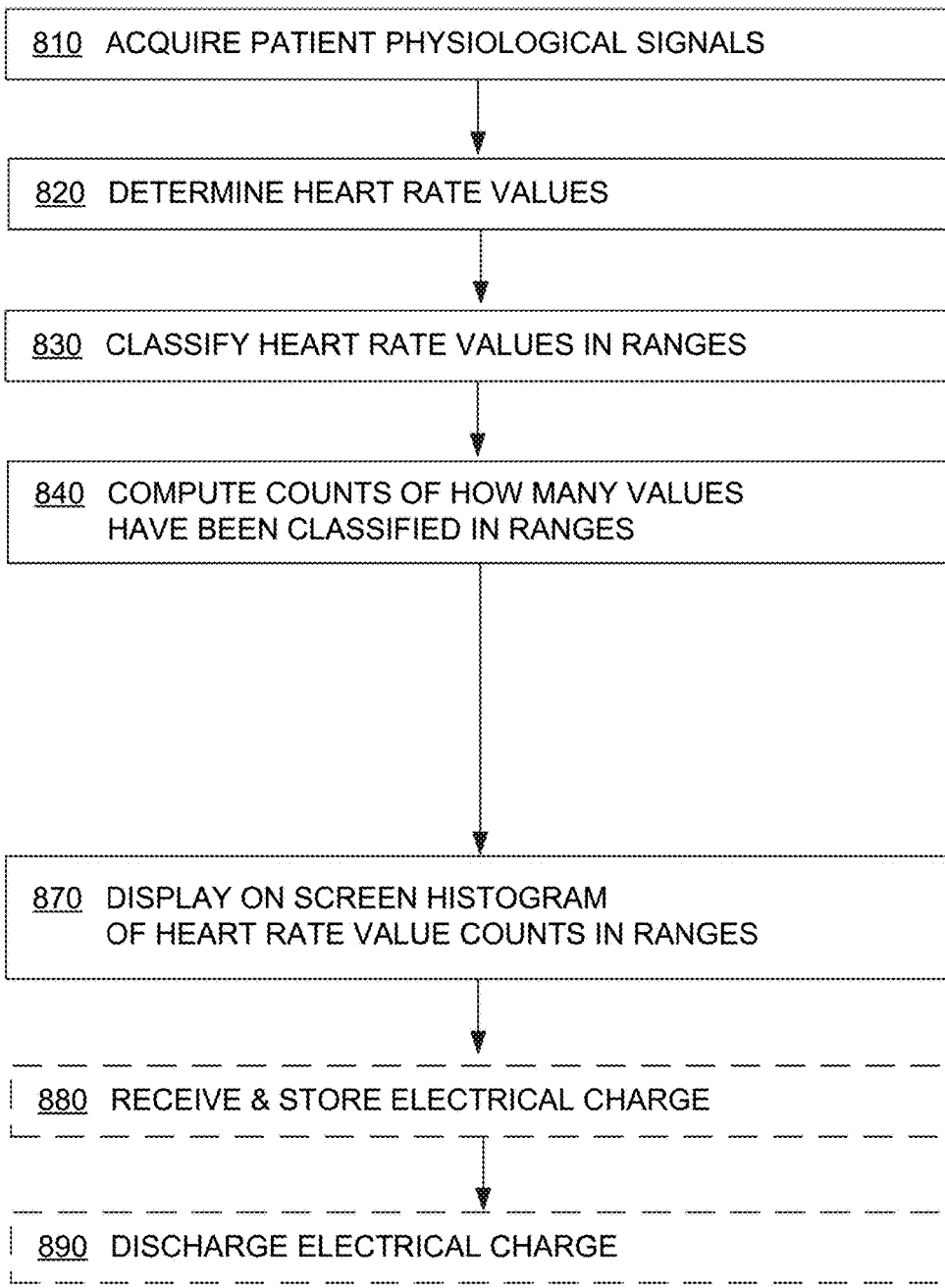
FIG. 8 is a flowchart for illustrating methods according to embodiments.

FIG. 8 shows a flowchart 800 for describing methods according to embodiments. According to an operation 810, patient physiological signals may be acquired by one or more sensors of a WCD system, while the patient is wearing the support structure of the WCD system. As mentioned previously, these patient physiological signals may include electrocardiogram (ECG) data of the patient, and/or other data of the patient.

According to another operation 820, heart rate values for heart rates may be determined from the acquired patient physiological signals, over a time interval.

According to another operation 830, at least some of the determined heart rate values may be classified as belonging in respective ranges of possible heart rate values.

According to another operation 840, a count may be computed for each one of the ranges. The count can be of how many of the determined heart rate values have been classified within that range.

According to another operation 870, there may be displayed, on the screen, as a histogram: a) indications of at least some of the ranges arrayed along a horizontal time axis, together with b) the respective counts of at least some of the ranges, illustrated along a vertical time axis. The result may appear similar to histogram 700.

In addition, different versions of histogram 700 may be thus displayed at different times. Data files can be stored in a memory, which encode the different versions of histogram 700. Plus, time stamps can be further stored in the memory in association with the respective data files. An additional data file may thus become thus stored after the passage of a preset aggregation time, or after a preset number of heart rate values have been determined, or responsive to a user input being received from an input device, etc.

Other optional operations 880 and 890 can be as the previously described operations 680 and 690, respectively.

In some embodiments, a WCD system causes the patient's QRS width to be plotted against the heart rate. Examples are now described.

Figure 9:
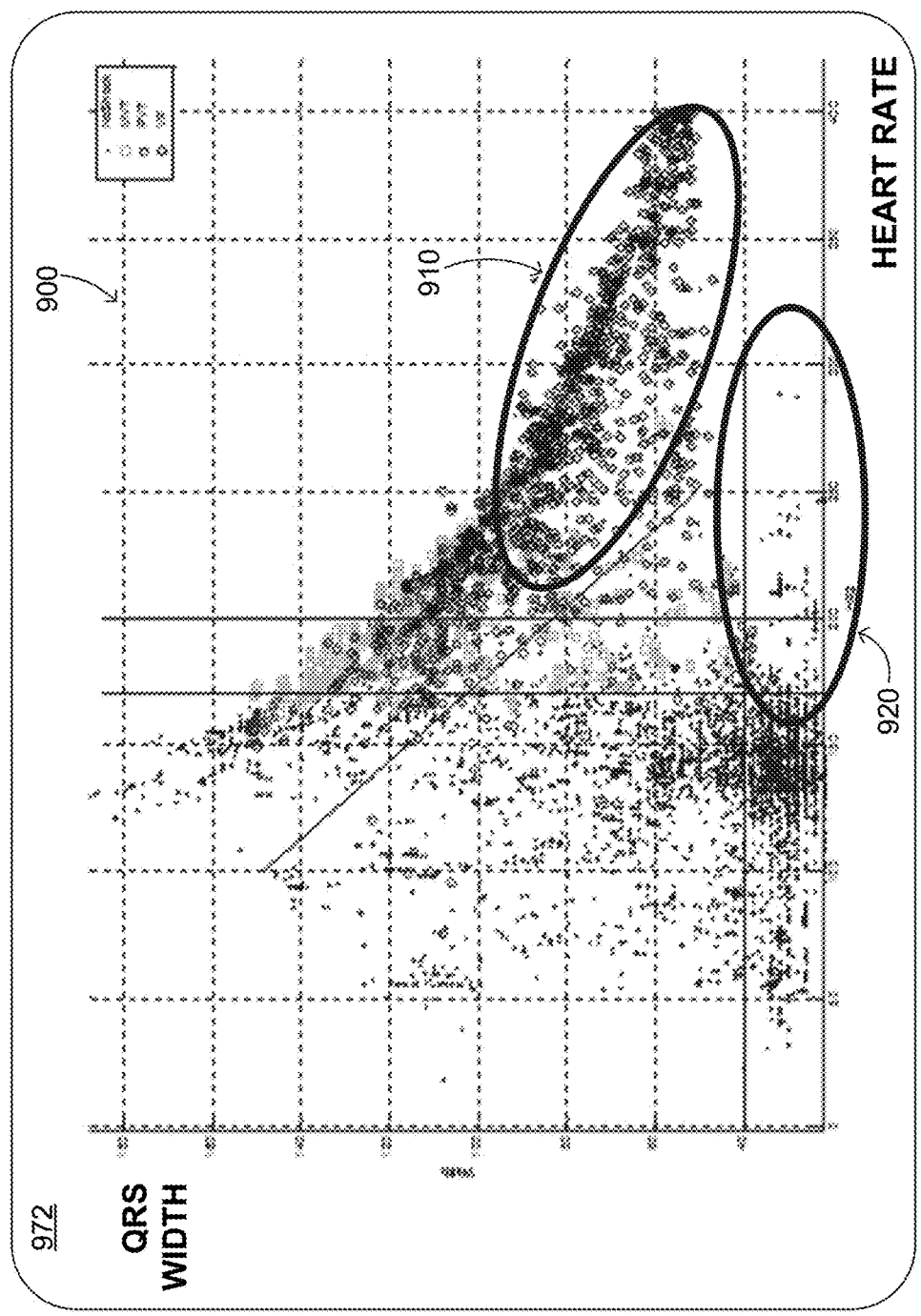
FIG. 9 is a diagram of a sample screen with a sample screenshot of a scatterplot graph of QRS width plotted against heart rate according to embodiments.

FIG. 9 is a diagram of a sample screen 972 with a sample screenshot. Sample screen 972 could be, for example, any one of previously described screens 272, 372, 373. The screenshot of sample screen 972 is a scatterplot diagram 900 of QRS width versus heart rate. On the horizontal axis there are heart rate values, from 0 to 400 bpm. On the vertical axis there are width values for a QRS complex, with intercepts provided for 40, 60, 80, . . . , 180 msec.

A diagram such as that of FIG. 9 enables review and classification of long durations of ECG recording. In this method, the data from short rhythm segments (e.g. 5 seconds) can be plotted as individual datapoints. With this, any rhythm segment falling within a zone of interest could be isolated. A first zone of interest 910 is where mostly VF occurs, which is a shockable rhythm. Another zone of interest 920 may indicate AF, AT (atrial tachycardia) or SVT. Rhythms that exceed the rate detection criteria but that are appropriately not classified by the algorithm as VT or VF may still be of clinical interest such as atrial fibrillation (AF). In this case, AF that conducts to the ventricle at high rates may necessitate pharmacologic intervention or ablation. ECG rhythm segments falling within zones of interest could be stored and presented to the clinician for further review.

Accordingly, in some embodiments the processor can be configured to select a plurality of aggregation periods within a time interval for which data has been acquired. The data may include ECG data. The time interval for the whole scatterplot can be any suitable duration, such as a day, or longer, a month, longer, and so on. The selected aggregation periods may or may not be of a duration similar to each other. In some embodiments, these aggregation periods are of a short duration, such as 5 sec.

Each of the aggregation periods may contribute a single point to the scatterplot. In particular, for each aggregation period, the processor may be configured to a) identify one or more QRS complexes of the ECG data within the aggregation period, b) render a representative width value for the identified one or more QRS complexes, and c) determine a representative heart rate value.

The rendered representative width value can be a value of an average width of the identified QRS complexes within the aggregation period. Or, it can be a value of a width of one of the identified QRS complexes within the aggregation period, if the aggregation interval is short enough and these widths do not change much during it. In the latter case, the rendered representative width value can be the value of the width of the first identified QRS complex within the aggregation period, or the last, etc.

Moreover, the representative heart rate value can be determined as a statistic of determined heart rate values within the aggregation period. Such a statistic can be an average, a median, etc. of instantaneous heart rate values determined from heart beats within the aggregation period. In particular, the time distance between two heart beats can be taken as an inverse of the heart rate, etc.

In such embodiments, the memory can be configured to store, for at least some of the aggregation periods, the rendered representative width values in association with the determined representative heart rate values, in other words as pairs.

Then the screen can be configured to display a plot of the stored width values against the associated stored heart rate values. The result could be scatterplot 900 of FIG. 9.

In addition, previous versions of such plots can be stored, for replay and review. More particularly, different versions of plot 900 can be displayed on screens 272, 372, 373 at different times. Memory 1938 can be configured to store data files 901, 902, 903, . . . that encode the different versions of plot 900, with respective time stamps 977, etc.

Figure 10:
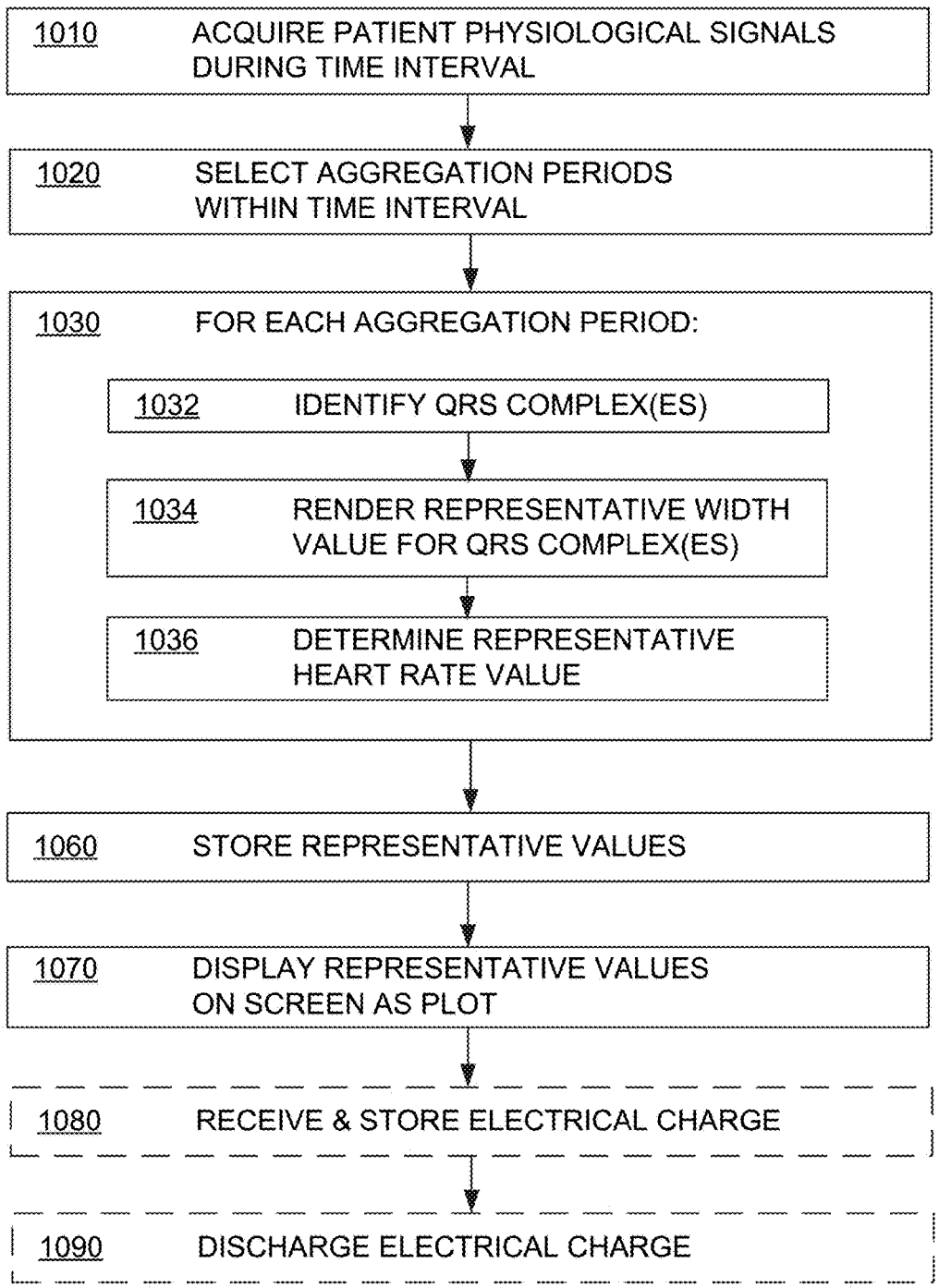
FIG. 10 is a flowchart for illustrating methods according to embodiments.

FIG. 10 shows a flowchart 1000 for describing methods according to embodiments. According to an operation 1010, there are acquired, by the one or more sensors, during a time interval patient physiological signals that include electrocardiogram (ECG) data of the patient. This may take place while the patient is wearing the support structure According to another, optional operation 1020, aggregation periods within the time interval may be selected.

Another operation 1030 may be performed for each aggregation period: according to an operation 1032, one or more QRS complexes of the ECG data may be identified within the aggregation period. Such may be by signal processing, etc. According to another, optional operation 1034, a representative width value may be rendered for the identified one or more QRS complexes. According to another, optional operation 1036, a representative heart rate value may be determined.

According to another, optional operation 1060, for at least some of the aggregation periods, the rendered representative width values may be stored in association with the determined representative heart rate values.

According to another, optional operation 1070, there may be displayed, on the screen, a plot of the stored width values against their associated stored heart rate values. The result could be scatterplot 900 of FIG. 9.

In addition, different versions of plot 900 may be thus displayed at different times. Data files can be stored in a memory, which encode the different versions of plot 900. Plus, time stamps can be further stored in the memory in association with the respective data files. An additional data file may thus become thus stored after the passage of a preset aggregation time, or after a preset number of representative heart rate values (equivalently, QRS widths or data points) have been determined, or responsive to a user input being received from an input device.

Other optional operations 1080 and 1090 can be as the previously described operations 680 and 690, respectively.

In some embodiments, a wearable cardioverter defibrillator (WCD) may cause heart rate trends of the patient to be displayed. Examples are now described.

Figure 11:
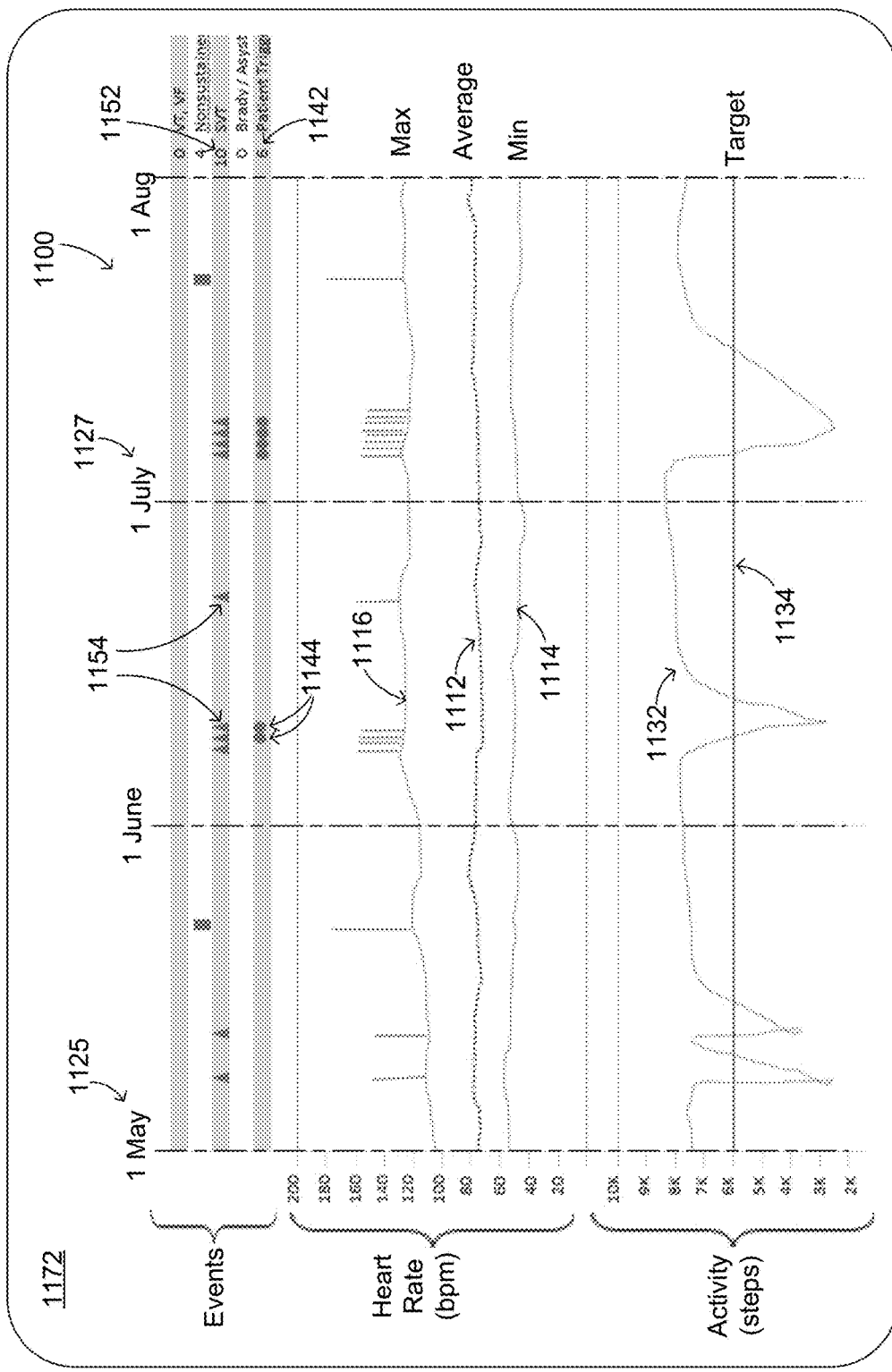
FIG. 11 is a diagram of a sample screen with a sample screenshot of a time diagram showing sample long term heart rate trends and other trends generated according to embodiments.

FIG. 11 is a diagram of a sample screen 1172 with a sample screenshot. Sample screen 1172 could be, for example, any one of previously described screens 272, 372, 373. The screenshot of sample screen 1172 is a time diagram 1100 generated according to embodiments. In diagram 1100, time proceeds along a horizontal direction, although there is no explicit time axis. In the vertical time axis there are three main quantities depicted, although a different combination may be used for embodiments.

In such embodiments, the processor can be configured to determine heart rate values from the acquired patient physiological signals for the time interval during which statistics will be monitored. The time interval can be one week or longer than one week, one month or longer, etc. For the example of FIG. 11, the time interval is 3 months (May, June and July). The data for each data point within the trend, however, will be aggregated over a much shorter aggregation period. In fact, the aggregation period can be at least 5 times shorter than the time interval, for example a single day compared to a whole month.

The processor may be further configured to render, from the heart rate values, representative values for respective aggregation periods within the time interval, the representative values being for a least one of a) average heart rates (seen as trend line 1112) of the patient, b) minimum heart rates (seen as trend line 1114) of the patient, and c) maximum heart rates (seen as trend line 1116) of the patient during the respective aggregation period. The represented values can be rendered by a statistic, such as averaging, mean, median, first, etc. In some embodiments, the resting heart rate could be derived during periods of low accelerometer activity, or the average day and night heart rates could be derived in association with corresponding time periods.

In such embodiments, the screen can be configured to display, along the horizontal direction, a trend diagram (1112, and/or 1114, and/or 1116) of the rendered representative values for at least a portion of the time interval.

The aggregation period is time during which data is collected. For some embodiments, a good value for the aggregation period is 1 hour, or a few hours. In some embodiments, the aggregation period is one day; a challenge is that the patient may have even taken off the WCD system for a day. In such embodiments, the rendered representative values further become associated with dates belonging to the time interval. Moreover, indicators 1125, 1127 for at least two of dates (1 May, 1 July) can be further displayed along the horizontal direction.

In some embodiments, activity is also determined by the proxy of counting steps. For example, the WCD system may further include a memory, and its one or more sensors may include a motion detector coupled to the support structure and configured to count steps of the patient. In such embodiments, values can be stored in the memory for the steps that are counted during at least some of the aggregation periods, and the stored values for the counted steps can be further displayed on the screen as a trend 1132 along the horizontal direction. In addition, a target value 1134 may be displayed.

In some embodiments, usage of trigger 271 may be tracked. For example, the WCD system may further include a memory. In such embodiments, the processor can be further configured to determine a total number of times that the trigger was actuated during the time interval, and values can be stored in the memory for the total number of times that the trigger was actuated during the time interval. Moreover, the screen can be further configured to display the stored total number of times 1142 that the trigger was actuated during the time interval.

In addition, the times that the trigger was actuated can be displayed together with the other trends. For example, the processor can be further configured to register moments that the trigger was actuated, and the memory can be configured to store values for the registered moments. In such embodiments, the screen can be further configured to display, along the horizontal direction, indicators 1144 for the registered moments that the trigger was actuated. Such information may help to correlate symptoms with arrhythmias.

In some embodiments, clinical events can be further counted. For example, the processor of the WCD system can be further configured to detect, from the acquired patient physiological signals, a certain clinical episode of the patient occurring during the time interval. The certain clinical episode can be any one of a Ventricular Fibrillation (VF) event, a Ventricular Tachycardia (VT) event, a SupraVentricular Tachycardia (SVT) event, a treated tachycardia event, an untreated tachycardia event, a Bradycardia (BC) event and an Asystole (AS) event, and so on. In such embodiments, the memory can be configured to increment a clinical counter value associated with the certain clinical episode responsive to the processor so detecting, and the screen can be further configured to display the incremented clinical counter value 1152.

In some embodiments, clinical events can be further correlated with the other monitored trends, in lieu of or in addition to being counted. For example, the processor can be further configured to register a time that the clinical episode occurred, and the memory can be configured to store a value for the registered time. In such embodiments, the screen can be further configured to display, along the horizontal direction, one or more indicators 1154 for the registered time. Such information may help to correlate symptoms with arrhythmias. Indicators 1154 can be plotted in accordance with time stamps for clinical events.

Figure 12:
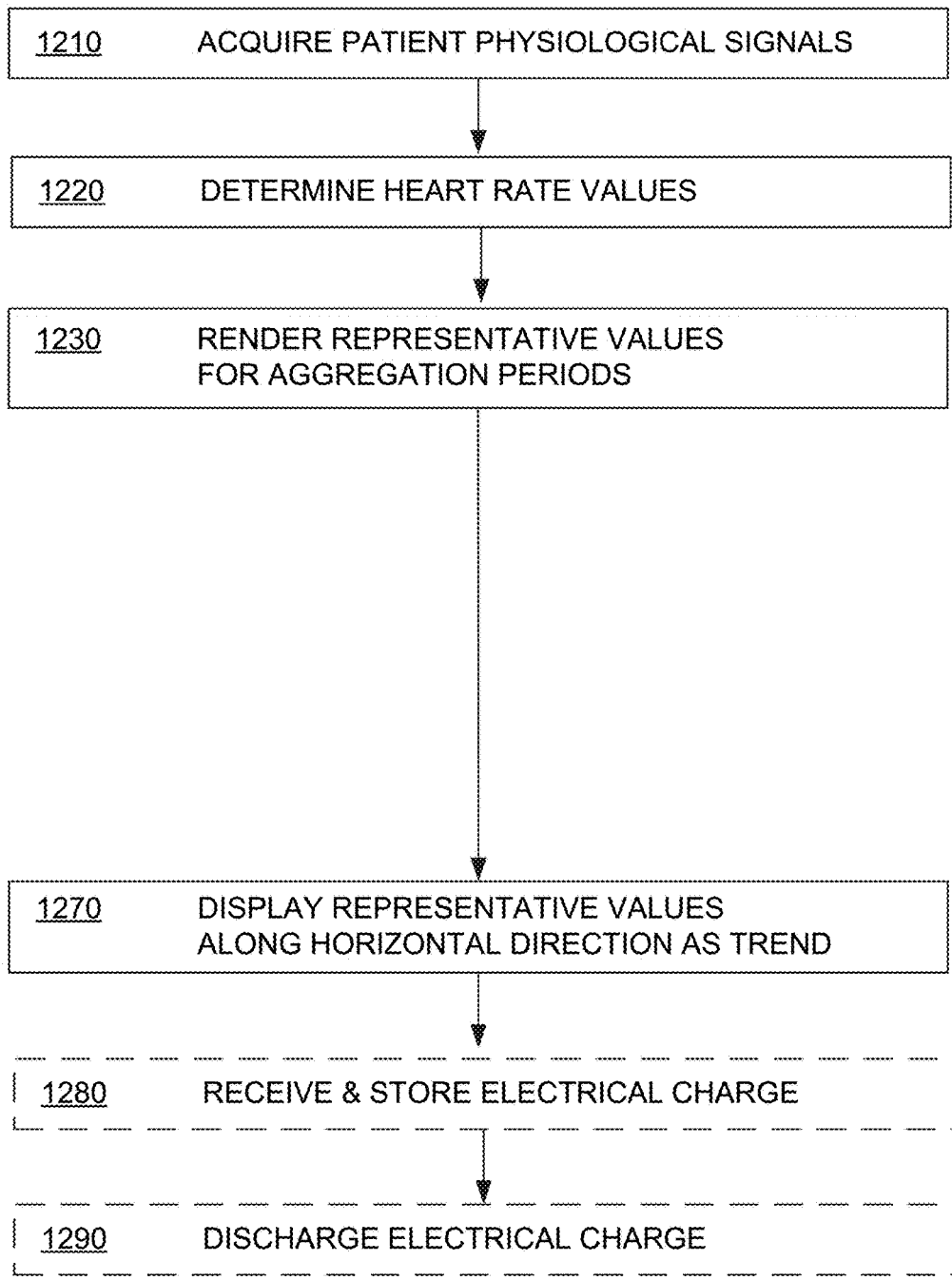
FIG. 12 is a flowchart for illustrating methods according to embodiments.

FIG. 12 shows a flowchart 1200 for describing methods according to embodiments. According to an operation 1210, patient physiological signals may be acquired for a time interval by the one or more sensors of a WCD system. The signals may be acquired while the patient is wearing the support structure.

According to another operation 1220, heart rate values may be determined by the processor, from the acquired patient physiological signals for the time interval.

According to another operation 1230, representative values may be rendered from the heart rate values. The representative values may be rendered for respective aggregation periods within the time interval. Each aggregation period may be at least 5 times shorter than the time interval. The representative values can be for a least one of a) average heart rates of the patient, b) minimum heart rates of the patient, and c) maximum heart rates of the patient during the respective aggregation period.

According to another, optional operation 1270, there may be displayed on the screen, along a horizontal direction, a trend diagram of the rendered representative values for at least a portion of the time interval. The result may be a graph such as that of FIG. 11.

Other optional operations 1280 and 1290 can be as the previously described operations 680 and 690, respectively.

In some embodiments, a wearable cardioverter defibrillator (WCD) may cause clinical event counters can be displayed. Some examples were shown above, and more examples are now described.

Figure 13:
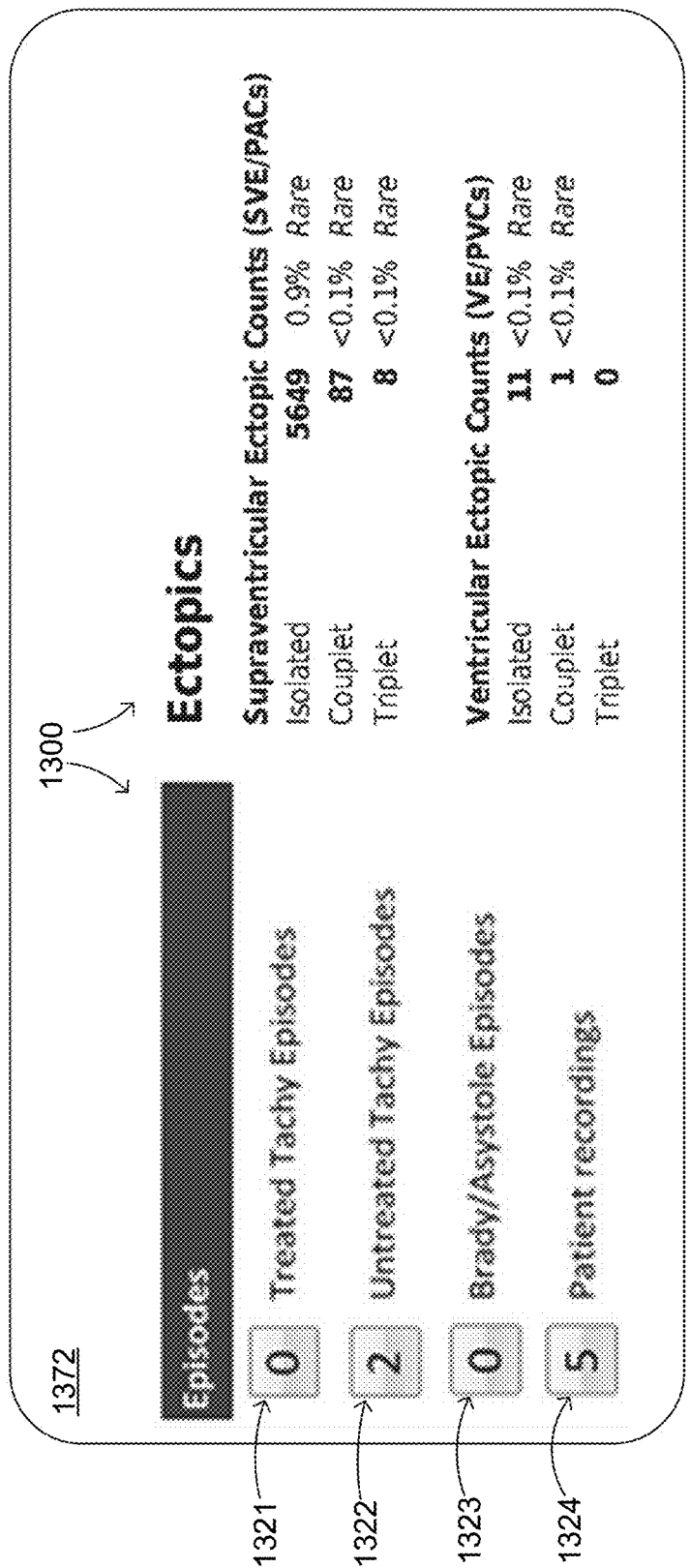
FIG. 13 is a diagram of a sample screen with a sample screenshot of a sample view of how clinical event counters may appear according to embodiments.

FIG. 13 is a diagram of a sample screen 1372 with a sample screenshot. Sample screen 1372 could be, for example, any one of previously described screens 272, 372, 373. The screenshot of sample screen 1372 is sample of tables 1300 for clinical event counters 1321, 1322, 1323, 1324 and others. In the results depicted, the tachy episodes and/or attributes of the ECG rhythm such as events of ectopic beats are thus presented to the user. The results may be counted over the total prescription and/or reset after seminal events such as drug regimen changes to set a new baseline.

In some embodiments, therefore, the processor can be configured to detect, from the acquired patient physiological signals, a certain clinical episode of the patient. The certain clinical episode could be of different event types. Such event types can include Ventricular Fibrillation (VF) events, Ventricular Tachycardia (VT) events, SupraVentricular Tachycardia (SVT) events, treated tachycardia events, untreated tachycardia events, Bradycardia (BC) events, Asystole (AS) events, isolated supraventricular ectopic events, couplet supraventricular ectopic events, triplet supraventricular ectopic events, isolated ventricular ectopic events, couplet ventricular ectopic events, triplet ventricular ectopic events, and so on.

Accordingly, the processor can monitor for events of a first event type, a second event type, a third event type, and so on. In some embodiments, the memory of the WCD system can be configured to maintain counters for the different event types. Plus, the processor can be configured to increment the counter values that are stored in the memory responsive to detecting events of the appropriate event type. Some of these episodes involve treatment, and therefore the appropriate clinical counter may be updated depending on whether or not treatment was administered or not.

And the screen can be configured to display the incremented clinical counter values as it does for the 10 counters in tables 1300. Moreover, for six of the counters, percentages are further computed, and so on.

In some embodiments, a time stamp is also captured. More particularly, responsive to the processor detecting the clinical event, a time stamp can be further captured and stored in the memory in association with the incrementing of the clinical counter value, or of a second clinical counter value, and so on.

At the time of the event, optionally values of other counters can be captured in association with the time stamp. For example, responsive to the processor detecting the second clinical event, the first clinical counter value, as last incremented, can also be stored in the memory in association with the time stamp. Such may permit displaying the progression of counts as a function of time. Some of that was seen as indicator 1154. Plus, trend diagrams can be created for multiple counter values at once, etc.

In other embodiments, some or all of the counters can be provided in duplicate. If there are more than one duplicate counters, the system can be thought of having two banks of counters. In some embodiments, therefore, tables 1300 would be provided in duplicate. An input device could permit a physician to initialize the counters in one bank, so as to track the counts of a single event from a specific baseline, without disturbing the longer term counts.

Figure 14:
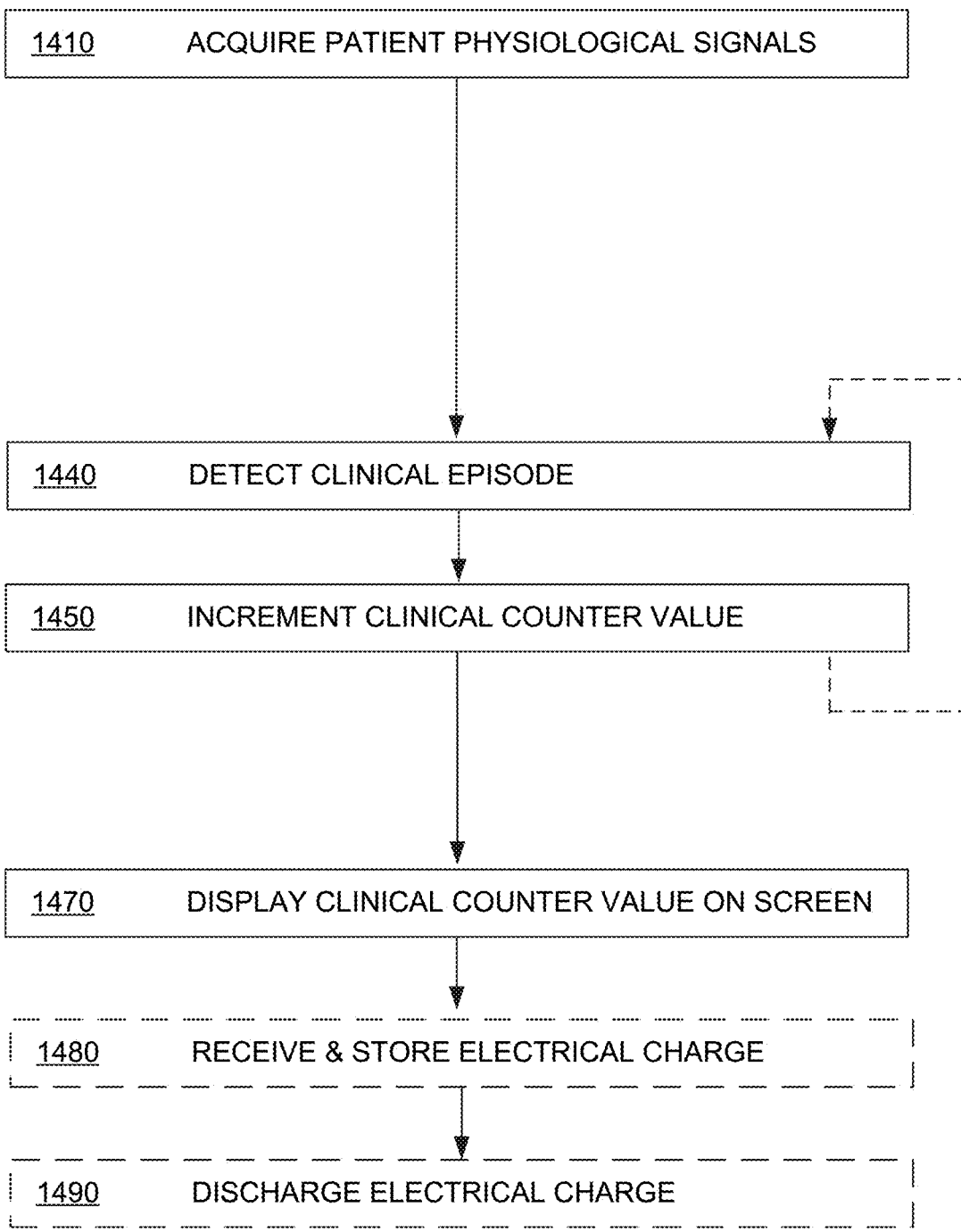
FIG. 14 is a flowchart for illustrating methods according to embodiments.

FIG. 14 shows a flowchart 1400 for describing methods according to embodiments. According to an operation 1410, there may be acquired, by the one or more sensors of a WCD system, patient physiological signals while the patient is wearing the support structure.

According to another operation 1440, a certain clinical event may be detected from the patient physiological signals acquired in operation 1410. The clinical event can be of an event type as described above.

According to another operation 1450, there can be incremented, responsive to operation 1440, a clinical counter value associated with the detected event type. A time stamp may be generated, etc.

Execution may then return to operation 1440, before the time interval is completed, according to the dashed line. Similarly, additional clinical counters may be incremented for different types of episodes, some of which may involve treatment, and so on.

According to another operation 1470, at monitoring time, the incremented clinical counter value may be displayed on the screen. If additional values are so displayed, then the display may appear as tables 1300.

Other optional operations 1480 and 1490 can be as the previously described operations 680 and 690, respectively.

In some embodiments, a wearable cardioverter defibrillator (WCD) may cause diagnostics related to patient's heart rate variability to be displayed. Examples are now described.

Figure 15:
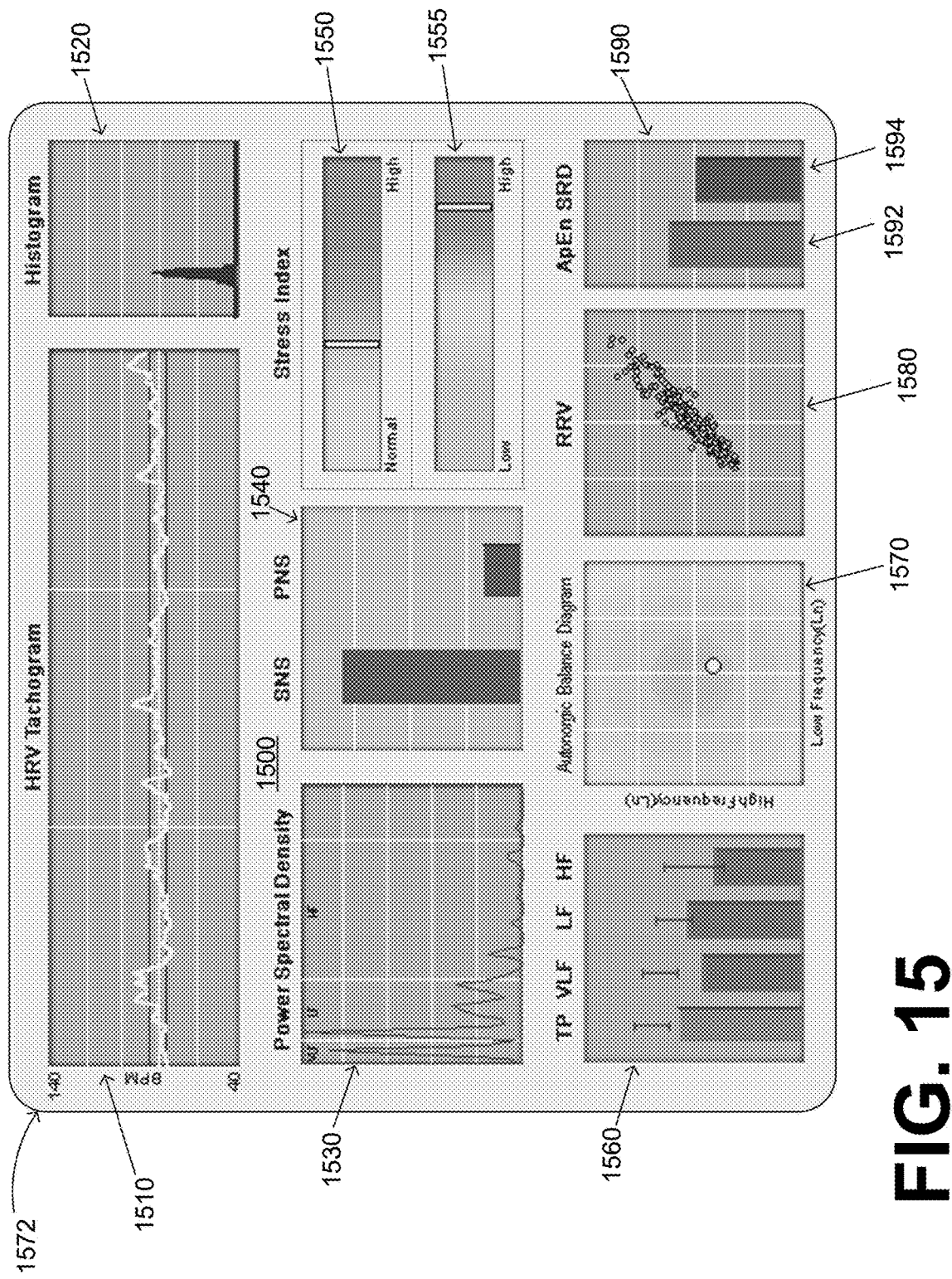
FIG. 15 is a diagram of a sample screen with a sample screenshot of a composite display for indicating diagnostics that are related to the patient's heart rate variability according to embodiments.

FIG. 15 is a diagram of a sample screen 1572 with a sample screenshot. Sample screen 1572 could be, for example, any one of previously described screens 272, 372, 373. The screenshot of sample screen 1572 is a composite display 1500, which is made by assembling together individual displays 1510, 1520, 1530, 1540, 1550, 1555, 1560, 1570, 1580 and 1590. These individual displays indicate respective sample diagnostics of information useful for measuring or depicting heart rate variability (HRV). There are many parameters that may used to assess heart rate variability (HRV). However, assessment of heart rate variability (HRV) most commonly involves the measure of the standard deviation of beat to beat intervals, typically measured from one P wave to the next and abbreviated as "SDNN".

Heart rate variability (HRV) is the physiological phenomenon of variation in the time interval between heartbeats. For example, as seen in FIG. 5, beat-to-beat intervals BB1, BB2, BB3 do not have the same "length" on the time axis, or duration. Heart rate variability (HRV) is measured by the variation in the beat-to-beat interval. Other terms for heart rate variability (HRV) include: "cycle length variability," "RR variability" (where R is a point corresponding to the peak of the QRS complex of the ECG wave; and RR is the interval between successive Rs—see FIG. 5), and "heart period variability."

Variation in the beat-to-beat interval is a physiological phenomenon. The SA node receives several different inputs and the instantaneous heart rate or RR interval and its variation are the results of these inputs. The main inputs are the sympathetic and the parasympathetic nervous system (PSNS) and humoral factors. Respiration gives rise to waves in heart rate mediated primarily via the PSNS, and it is thought that the lag in the baroreceptor feedback loop may give rise to 10 second waves in heart rate (associated with Mayer waves of blood pressure), but this remains controversial.

Factors that affect the input are the baroreflex, thermoregulation, hormones, sleep-wake cycle, meals, physical activity, and stress. Decreased PSNS activity or increased SNS activity will result in reduced HRV. High frequency (HF) activity (0.15 to 0.40 Hz), especially, has been linked to PSNS activity. Activity in this range is associated with the respiratory sinus arrhythmia (RSA), a vagally mediated modulation of heart rate such that it increases during inspiration and decreases during expiration. Less is known about the physiological inputs of the low frequency (LF) activity (0.04 to 0.15 Hz). Though previously thought to reflect SNS activity, it is now widely accepted that it reflects a mixture of both the SNS and PSNS.

Consider also heart rate variability phenomena. There can be are two primary fluctuations. First, respiratory arrhythmia (or respiratory sinus arrhythmia) may occur. This heart rate variation is associated with respiration and faithfully tracks the respiratory rate across a range of frequencies. Additionally, low-frequency oscillations may occur. This heart rate variation is associated with Mayer waves (Traube-Hering-Mayer waves) of blood pressure and is usually at a frequency of 0.1 Hz or a 10-second period.

In embodiments, therefore, a processor of the WCD system can be configured to identify, from the patient physiological signals, heart beats of the patient over a time interval. The time interval can be a week, a month, longer, and so on. Methods used to detect heart beats include, as also mentioned earlier in this document: ECG, blood pressure, ballistocardiograms, and the pulse wave signal derived from a photoplethysmograph (PPG). ECG is considered superior because ECG provides a clear waveform, which makes it easier to exclude heartbeats not originating in the sinoatrial node. The term "NN" may be used in place of RR to emphasize the fact that the processed beats are "normal" heart beats.

In embodiments, therefore, a processor of the WCD system can be further configured to detect time delays between successive ones of the identified heart beats. These time delays correspond closely to the beat-to-beat intervals seen in FIG. 5. Another name for them is RR-interval.

The processor may be further configured to derive one or more values from the detected time delays. These values can be simply the values of the time delays (e.g. RR-interval in msec), or statistics from them, and so on.

The processor can be moreover configured to correlate the one or more derived values with one or more parameter values of an other parameter. As will be seen, there can be many examples of other parameters, such as time, other variables, or even versions of the one or more values derived from the detected time delays. In such embodiments, then, the screen can be configured to display a graph that depicts the one or more derived values as correlated with the one or more parameter values.

In some embodiments, the other parameter is time. In such cases a value can be plotted in a time diagram. In some of these embodiments, the derived values are measures of the detected time delays, the graph is a time diagram of the derived values. An example is individual display 1510, which is also known as an HRV tachogram. The HRV tachogram presents the fluctuation (up and down) of heart rate during 5 minutes, as may have been influenced by constant ANS regulation on heart.

In some embodiments, the derived values are measures of the detected time delays, the other parameter is a frequency of occurrence of the measures of the detected time delays, and the graph is a histogram. An example is individual display 1520, where X-scale indicates RR-interval (msec) while Y scale indicates the number of heart rate (bpm) recorded. Lowered HRV is likely to draw a histogram with narrow width and high peak while higher HRV accompanies that with flattish shape without prominent peak.

In some embodiments, the other parameter values are frequency values. In some embodiments, a graph can be a graph of power spectral density (PSD) with reference to heart rates at different frequency ranges. An example is individual display 1530, which is a line graph that depicts power spectral density (PSD). The X axis indicates frequency (Hz) and Y axis indicates power (msec$^2$/Hz). PSD is power spectrum of, say, a 5-minute heart rate variability waveform of tachogram such as the one of display 1510. PSD analysis provides information about how power is distributed in each frequency-section, VLF, LF and HF.

In some embodiments, the graph is a graph of a sympathetic nervous system (SNS) activity of the patient. In some embodiments, the graph is a graph of a parasympathetic nervous system (PNS) activity of the patient. An example of both is individual display 1540. In fact, individual display 1540 further indicates a balance between the SNS activity and the PNS activity of the patient, as the two bar charts add up to 100%.

In some embodiments, the parameter value is a standard deviation of the measured time delays.

In some embodiments, the graph is a graph of a physical pressure index reflecting a standard deviation of a certain number (NN) of intervals in the time interval. An example is individual display 1550, which shows physical pressure index reflecting the SDNN and HRT in time domain. If the vertical white bar goes to high side towards the right of the drawing, it means that the pressure to the heart gets higher. An individual with higher level of physical pressure is more likely to have psychosomatic disorder.

Individual display 1555 reflects emotional status, and may be derived from the balance between SNS and PNS. Although the balance of the two charts is not the sole factor associated with individual's emotional status, this display 1555 may give some useful clues. For instance, the feeling of anger or anxiety can move the vertical white bar to 'high (hyper-arousal)' side indicating SNS dominant to PNS while the feeling of appreciation may move the bar to 'low (hypo-arousal)' side indicating PNS dominant to SNS.

Individual display 1560 is a bar graph depiction of total power (TP), very low frequency (VLF), low frequency (LF) and high frequency (HF). Here, Total Power (TP) may be derived as a combination of the VLF, LF and HF. The total power (TP) can be an indicator of general activity of autonomic nervous system and sympathetic nervous system as basic factor. Chronic stress and disease may decrease the total power due to the weakened regulating function. TP may have similar meaning with SDNN in a time domain analysis. The VLF (Very Low Frequency) provides complementary information about the sympathetic nervous system, and in a frequency band of 0.0033-0.04 Hz. The LF (Low Frequency) can be an indicator of sympathetic/parasympathetic nervous system, and in a frequency band of 0.04-0.15 Hz. The HF (High Frequency) can be an indicator of parasympathetic nervous system, and in a frequency band of 0.15-0.4 Hz.

In some embodiments, the graph can be a graph of an autonomic balance diagram (ABD) of the patient. An example is individual display 1570, in which works as a shaded plot. In this example, the X-axis indicates LF power (log value); a sympathetic condition. The Y-axis indicates HF power (log value); a parasympathetic condition. The area in the center of diagram is the ideal zone. In this example, the dot is close to the center of the diagram, indicating a rather healthy balance.

In some embodiments, the one or more derived values reflect measures of the detected time delays, and the one or more parameter values are the previously computed respective one or more derived values. In some of these versions, the time delays can be compared with previous time delays to detect their variation (RRV). An example is individual display 1580, which is a scatterplot. RRV indicates RR variation which reflects the variability of the heart rate. The RRV scatterplot looks like a "cloud" which consists of a number of points. RRV graphically displays current heart rate variability value versus the previous value. In other words, abscissa of the point is the length of the previous NN interval. The more variation that exist in the HRT, the wider the "cloud" (dotted shape) is displayed. If the heart rate were monotonously regular, the "cloud" would be the shape of a small and round ball with great density, rather than long oval shape.

In some embodiments, the graph depicts an approximate entropy (ApEn). In some embodiments, the one or more parameter values are time differences between successive ones of the detected time delays (SRD). An example of both is individual display 1590.

Bar 1592 depicts ApEn, approximate entropy. This is statistic quantifying regularity and complexity that appears to have potential application to a wide variety of physiological and clinical time-series data. The higher ApEn (max. 2, the top of display 1590) is, the more tachogram is complex, which is considered good.

Bar 1594 (SRD) depicts successive R-R interval difference. The SRD may be calculated by comparing the initial part (⅓) of total measuring duration to the successive part (⅔) of total measuring duration. The value 1 (the mid-line height of display 1590) is the ideal state, which means that the measurement was done under constant status.

A substantial amount of information can be learned from heart rate variability (HRV).

For example, consider the clinical significance of HRV. Reduced HRV has been shown to be a predictor of mortality after myocardial infarction, although some research has shown that the information in HRV relevant to acute myocardial infarction survival is fully contained in the mean heart rate. A range of other outcomes/conditions may also be associated with modified (usually lower) HRV, including congestive heart failure, diabetic neuropathy, depression, post-cardiac transplant, etc.

Consider also the mental and social aspects of reduced HRV. In the field of psychophysiology, there is interest in HRV. For example, HRV is related to emotional arousal. High-frequency (HF) activity has been found to decrease under conditions of acute time pressure and emotional strain and elevated state anxiety, presumably related to focused attention and motor inhibition. HRV has been shown to be reduced in individuals reporting a greater frequency and duration of daily worrying. In individuals with post-traumatic stress disorder (PTSD), HRV and its HF component (see below) is reduced compared to controls whilst the low-frequency (LF) component is elevated. Furthermore, unlike controls, PTSD patients demonstrated no LF or HF reactivity to recalling a traumatic event.

The Polyvagal Theory derives from a psychophysiologic imputation of importance to HRV. This theory emphasizes the role of heart rate variability in understanding the magnitude and nature of vagal outflow to the heart. This theory decomposes heart rate variability based on frequency domain characteristics with an emphasis on respiratory sinus arrhythmia and its transmission by a neural pathway that is distinct from other components of HRV. There is anatomic and physiological evidence for a polyvagal control of the heart.

Errors in the location of the instantaneous heart beat will result in errors in the calculation of the HRV. HRV is highly sensitive to artifact and errors in as low as even two percent (2%) of the data will result in unwanted biases in HRV calculations. To ensure accurate results, therefore, artifact and R-R errors should be managed appropriately prior to performing any HRV analyses.

Robust management of artifact, including R wave identification, interpolation and exclusion requires a high degree of care and precision. This can be very time consuming in large studies with data recorded over long durations. Powerful and specialized software packages, such as VivoSense available from Vivonoetics of San Diego, Calif., are available to assist users with a variety of robust and tested artifact management tools. These software programs also include some automated capability but it is important that a human review any automated artifact management and edit accordingly.

HRV analysis can be performed with time-domain methods. Time-domain methods are based on the beat-to-beat or NN intervals, which are analyzed to give variables. HRV analysis can be performed with frequency-domain methods. Geometric methods may also be employed.

Examples of time-domain analysis variables include, without limitation: SDNN, the standard deviation of NN intervals, often calculated over a 24-hour period. SDANN, the standard deviation of the average NN intervals calculated over short periods, usually 5 minutes. SDANN is therefore a measure of changes in heart rate due to cycles longer than 5 minutes. SDNN reflects all the cyclic components responsible for variability in the period of recording, therefore it represents total variability. RMSSD ("root mean square of successive differences"), the square root of the mean of the squares of the successive differences between adjacent NNs. SDSD ("standard deviation of successive differences"), the standard deviation of the successive differences between adjacent NNs. NN50, the number of pairs of successive NNs that differ by more than 50 ms. pNN50, the proportion of NN50 divided by total number of NNs. NN20, the number of pairs of successive NNs that differ by more than 20 ms. pNN20, the proportion of NN20 divided by total number of NNs. EBC ("estimated breath cycle"), the range (max-min) within a moving window of a given time duration within the study period. The windows can move in a self-overlapping way or be strictly distinct (sequential) windows. EBC is often provided in data acquisition scenarios where HRV feedback in real time is a primary goal. EBC derived from PPG over 10-second and 16-second sequential and overlapping windows has been shown to correlate highly with SDNN.

Frequency domain methods assign bands of frequency and then count the number of NN intervals that match each band. The bands are typically high frequency (HF) from 0.15 to 0.4 Hz, low frequency (LF) from 0.04 to 0.15 Hz, and the very low frequency (VLF) from 0.0033 to 0.04 Hz. Several methods of frequency domain analysis are available. Power spectral density (PSD), using parametric or nonparametric methods, provides basic information on the power distribution across frequencies, such as the discrete Fourier transform. Methods for the calculation of PSD may be generally classified as nonparametric and parametric. In most instances, both methods provide comparable results. The advantages of the nonparametric methods are (1) the simplicity of the algorithm used (fast Fourier transform [FFT] in most of the cases) and (2) the high processing speed, while the advantages of parametric methods are (1) smoother spectral components that can be distinguished independent of preselected frequency bands, (2) easy post-processing of the spectrum with an automatic calculation of low-frequency and high-frequency power components with an easy identification of the central frequency of each component, and (3) an accurate estimation of PSD even on a small number of samples on which the signal is supposed to maintain stationarity. The basic disadvantage of parametric methods is the need of verification of the suitability of the chosen model and of its complexity (that is, the order of the model).

In addition to classical FFT-based methods used for the calculation of frequency parameters, a more appropriate PSD estimation method is the Lomb-Scargle (LS) periodogram. Analysis has shown that the LS periodogram can produce a more accurate estimate of the PSD than FFT methods for typical RR data. Since the RR data is an unevenly sampled data, another advantage of the LS method is that in contrast to FFT-based methods it is able to be used without the need to resample and detrend the RR data.

The series of NN intervals also can be converted into a geometric pattern such as the sample density distribution of NN interval durations, sample density distribution of differences between adjacent NN intervals, Lorenz plot of NN or RR intervals, and so forth, and a simple formula may be used that judges the variability on the basis of the geometric and/or graphics properties of the resulting pattern.

Given the complexity of the mechanisms regulating heart rate, it is reasonable to assume that applying HRV analysis based on methods of non-linear dynamics will yield valuable information. Although chaotic behavior has been assumed, more rigorous testing has shown that heart rate variability cannot be described as a low dimensional chaotic process. However, application of chaotic globals to HRV has been shown to predict diabetes status.

Heart rate variability may be analyzed by the non-linear method of a Poincaré plot. Each data point represents a pair of successive beats, the x-axis is the current RR interval, while the y-axis is the previous RR interval. HRV can be quantified by fitting mathematically defined geometric shapes to the data. Other methods that may be used are the correlation dimension, nonlinear predictability, pointwise correlation dimension, de-trended fluctuation analysis, approximate entropy, sample entropy, multiscale entropy analysis, sample asymmetry and memory length (based on inverse statistical analysis).

Time domain methods may be preferred to frequency domain methods when short-term recordings are investigated. This can be due to the fact that the recording should be at least 10 times the wavelength of the lowest frequency bound of interest. Thus, recording of approximately 1 minute is needed to assess the HF components of HRV (i.e., a lowest bound of 0.15 Hz is a cycle of 6.6 seconds and so 10 cycles require ~60 seconds), while more than 4 minutes are needed to address the LF component (with a lower bound of 0.04 Hz).

Although time domain methods, especially the SDNN and RMSSD methods, can be used to investigate recordings of long durations, a substantial part of the long-term variability is the variability arising between day and night measurements. Thus, it is preferred that long-term recordings analyzed by time domain methods contain at least 18 hours of analyzable ECG data that include the whole night.

The sympathetic influence on heart rate is mediated by release of epinephrine and norepinephrine. Activation of β-adrenergic receptors results in cAMP-mediated phosphorylation of membrane proteins and increases in ICaL and in If the end result is an acceleration of the slow diastolic depolarization.

Under resting conditions, vagal tone prevails and variations in heart period are largely dependent on vagal modulation. The vagal and sympathetic activity constantly interact. Because the sinus node is rich in acetylcholinesterase, the effect of any vagal impulse is brief because the acetylcholine is rapidly hydrolyzed. Parasympathetic influences exceed sympathetic effects probably through two independent mechanisms: (1) a cholinergically induced reduction of norepinephrine released in response to sympathetic activity and (2) a cholinergic attenuation of the response to an adrenergic stimulus.

The RR interval variations present during resting conditions represent beat-by-beat variations in cardiac autonomic inputs. However, efferent vagal (parasympathetic) activity is a major contributor to the HF component, as seen in clinical and experimental observations of autonomic maneuvers such as electrical vagal stimulation, muscarinic receptor blockade, and vagotomy. More problematic is the interpretation of the LF component, which may include both sympathetic and vagal influences. For example, during sympathetic activation the resulting tachycardia is usually accompanied by a marked reduction in total power, whereas the reverse occurs during vagal activation. Thus the spectral components change in the same direction and do not indicate that LF faithfully reflects sympathetic effects.

It is important to note that HRV measures fluctuations in autonomic inputs to the heart rather than the mean level of autonomic inputs. Thus, both withdrawal and saturatingly high levels of autonomic input to the heart can lead to diminished HRV.

Changes of HRV related to specific pathologies have been noted. A reduction of HRV has been reported in several cardiovascular and noncardiovascular diseases. Consider, for example, myocardial infarction (MI). Depressed HRV after MI may reflect a decrease in vagal activity directed to the heart. HRV in patients surviving an acute MI reveal a reduction in total and in the individual power of spectral components. The presence of an alteration in neural control is also reflected in a blunting of day-night variations of RR interval. In post-MI patients with a very depressed HRV, most of the residual energy is distributed in the VLF frequency range below 0.03 Hz, with only a small respiration-related variations.

Consider also diabetic neuropathy. In neuropathy associated with diabetes mellitus characterized by alteration in small nerve fibers, a reduction in time domain parameters of HRV seems not only to carry negative prognostic value but also to precede the clinical expression of autonomic neuropathy. In diabetic patients without evidence of autonomic neuropathy, reduction of the absolute power of LF and HF during controlled conditions was also reported. Similarly, diabetic patients can be differentiated from normal controls on the basis of reduction in HRV.

Myocardial dysfunction. A reduced HRV has been observed consistently in patients with cardiac failure. In this condition characterized by signs of sympathetic activation such as faster heart rates and high levels of circulating catecholamines, a relation between changes in HRV and the extent of left ventricular dysfunction was reported. In fact, whereas the reduction in time domain measures of HRV seemed to parallel the severity of the disease, the relationship between spectral components and indices of ventricular dysfunction appears to be more complex. In particular, in most patients with a very advanced phase of the disease and with a drastic reduction in HRV, an LF component could not be detected despite the clinical signs of sympathetic activation. This reflects that, as stated above, the LF may not accurately reflect cardiac sympathetic tone.

Liver cirrhosis. Liver cirrhosis is associated with decreased HRV. Decreased HRV in patients with cirrhosis has a prognostic value and predicts mortality. Loss of HRV is also associated with higher plasma pro-inflammatory cytokine levels and impaired neurocognitive function in this patient population.

Tetraplegia. Patients with chronic complete high cervical spinal cord lesions have intact efferent vagal neural pathways directed to the sinus node. However, an LF component can be detected in HRV and arterial pressure variabilities of some tetraplegic patients. Thus, the LF component of HRV in those without intact sympathetic inputs to the heart represent vagal modulation.

Figure 16:
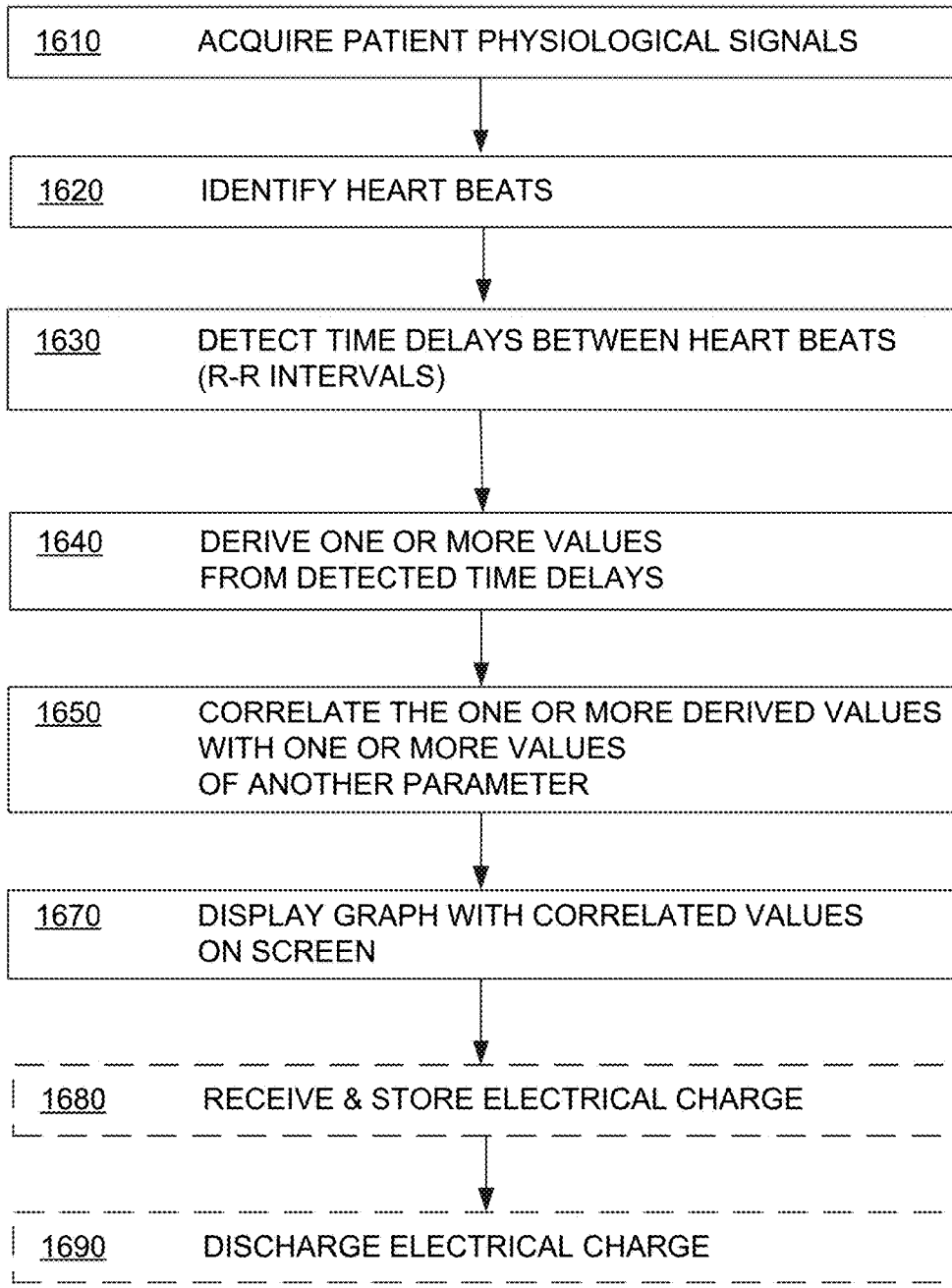
FIG. 16 is a flowchart for illustrating methods according to embodiments.

FIG. 16 shows a flowchart 1600 for describing methods according to embodiments. According to an operation 1610, patient physiological signals are acquired, similarly with similarly numbered operations.

According to another operation 1620, heart beats of the patient may be identified from the patient physiological signals, over a time interval.

According to another operation 1630, time delays between successive ones of the identified heart beats may be detected.

According to another operation 1640, one or more values may be derived from the detected time delays. These may establish the heart rate variability.

According to another operation 1650, the one or more derived values may be correlating with one or more parameter values of an other parameter. Examples were given above.

According to another operation 1670, there may be displayed, on a screen, a graph that depicts the one or more derived values as correlated with the one or more parameter values.

Other optional operations 1680 and 1690 can be as the previously described operations 680 and 690, respectively.

In some embodiments, a wearable cardioverter defibrillator (WCD) may cause be displayed diagnostics about the patient's atrial arrhythmia burden (AAB). Examples are now described.

Figure 17:
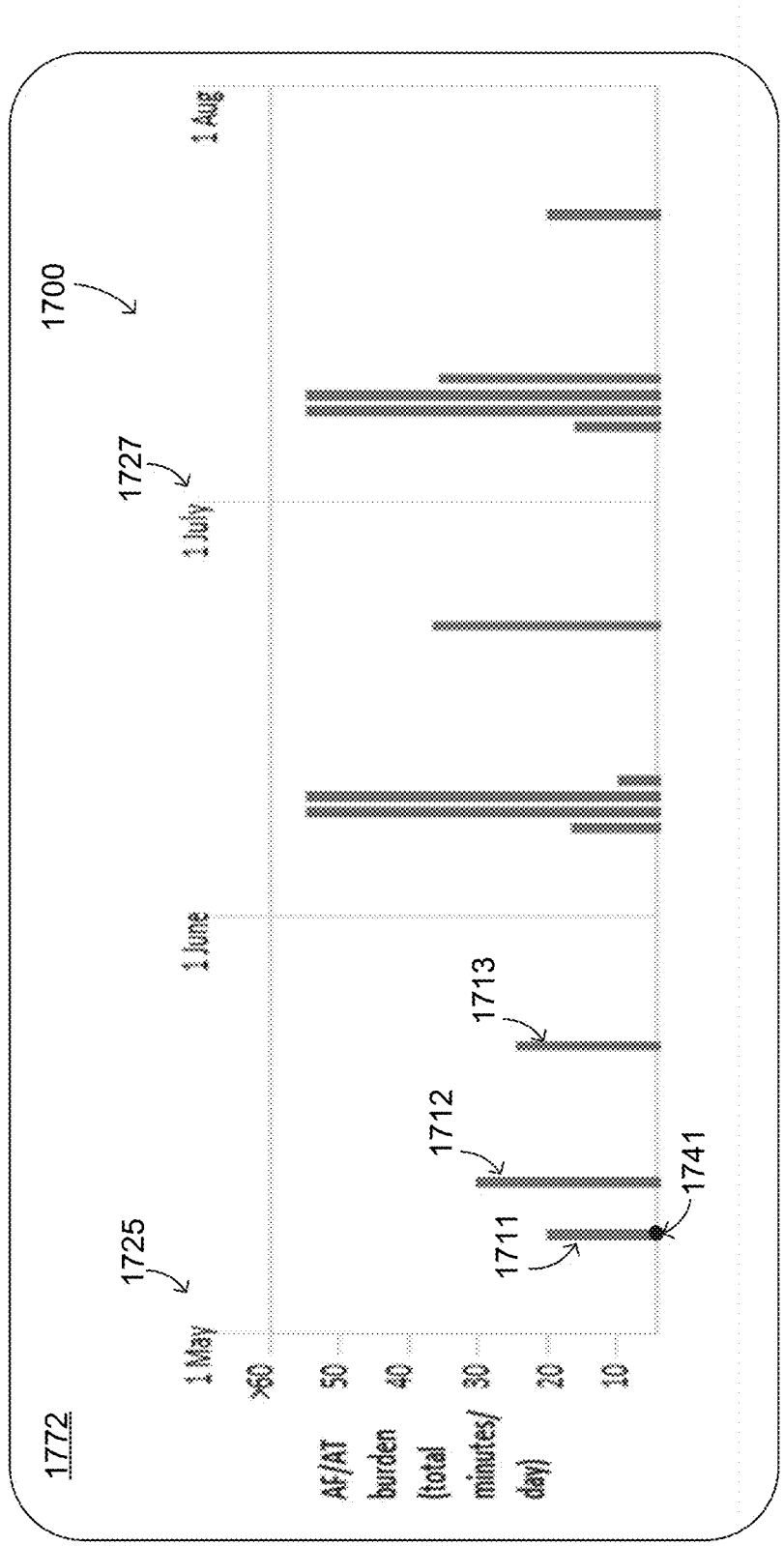
FIG. 17 is a diagram of a sample screen with a sample screenshot of a bar graph depicting a time distribution of an atrial arrhythmia burden for monitoring during a time interval according to embodiments.

FIG. 17 is a diagram of a sample screen 1772 with a sample screenshot. Sample screen 1772 could be, for example, any one of previously described screens 272, 372, 373. The screenshot of sample screen 1772 is a sample bar graph 1700. Bar graph 1700 depicts, over a time interval of 3 months, an AAB history and/or trend of the patient. In this example, the aggregation period has been one day, meaning daily results are shown. So, time is displayed along the horizontal direction, in units of days. A daily basis may also include a rolling 24 hour basis.

In graph 1700, the vertical axis shows a time value of a suffering duration during which the patient so suffered that day. In this case, the time values are on the scale of 10, 20, 30, . . . minutes.

In graph 1700, the first such day during which the patient so suffered is indicated as point 1741 in this diagram. A vertical bar 1711 is interpreted against the vertical axis, to indicate the determined time value of about 20 minutes.

The whole time interval spanned by graph 1700 includes additional aggregation periods of days, some of which have non-zero suffering durations. For those, additional indications 1712, 1713 are displayed, whose respective additional time values can be interpreted against by the vertical axis. As such, each successive day adds more data to the bar chart (i.e., tracking is on a daily basis).

Accordingly, graph 1700 depicts the amount of time the patient spent in atrial arrhythmia for the time interval. The term Atrial Arrhythmia Burden (AAB) may be used for the total in the time interval. Graph 1700 may be used help to assess the need to adjust the patient's pharmacologic therapies or interventions.

In such embodiments, graph 1700 may be useful to display together with the heart rate trends of FIG. 11 using a common time frame. For example, such may help correlate incidences of where the maximum heart rate was much higher with AAB. Plus, the AAB may further help explain why the patient was inclined to be a lot less active those days, at least as judged by the number of steps.

In such embodiments, then, the processor can be configured to determine, from the physiological signals, whether or not the patient suffered an atrial arrhythmia during an aggregation period, for example of day 1741. If so, the processor may further determine a time value of a suffering duration within the aggregation period during which the patient so suffered. And the screen may display an indication 1711 for the determined time value for the suffering duration.

In some of these embodiments, a whole trend is shown, such as in graph 1700. In particular, the processor is further configured to determine whether the patient so suffered for a time interval that lasts the aggregation period (e.g. day 1741) plus multiple additional aggregation periods (e.g. the indicated 3 months). If so, the processor may further determine for such respective additional aggregation periods respective additional time values of respective additional suffering durations during which the patient so suffered. And the screen may further display, along the horizontal direction, a trend diagram of respective additional indications 17112, 1713 for the determined respective additional time values for the time interval.

In some of these embodiments, the aggregation period is one day. In such embodiments, the respective additional aggregation periods further become associated with dates belonging to the time interval, for example the first day of May, June, July and August. In such embodiments, indicators 1725, 1727 for at least two of the associated dates can be further displayed along the horizontal direction.

Figure 18:
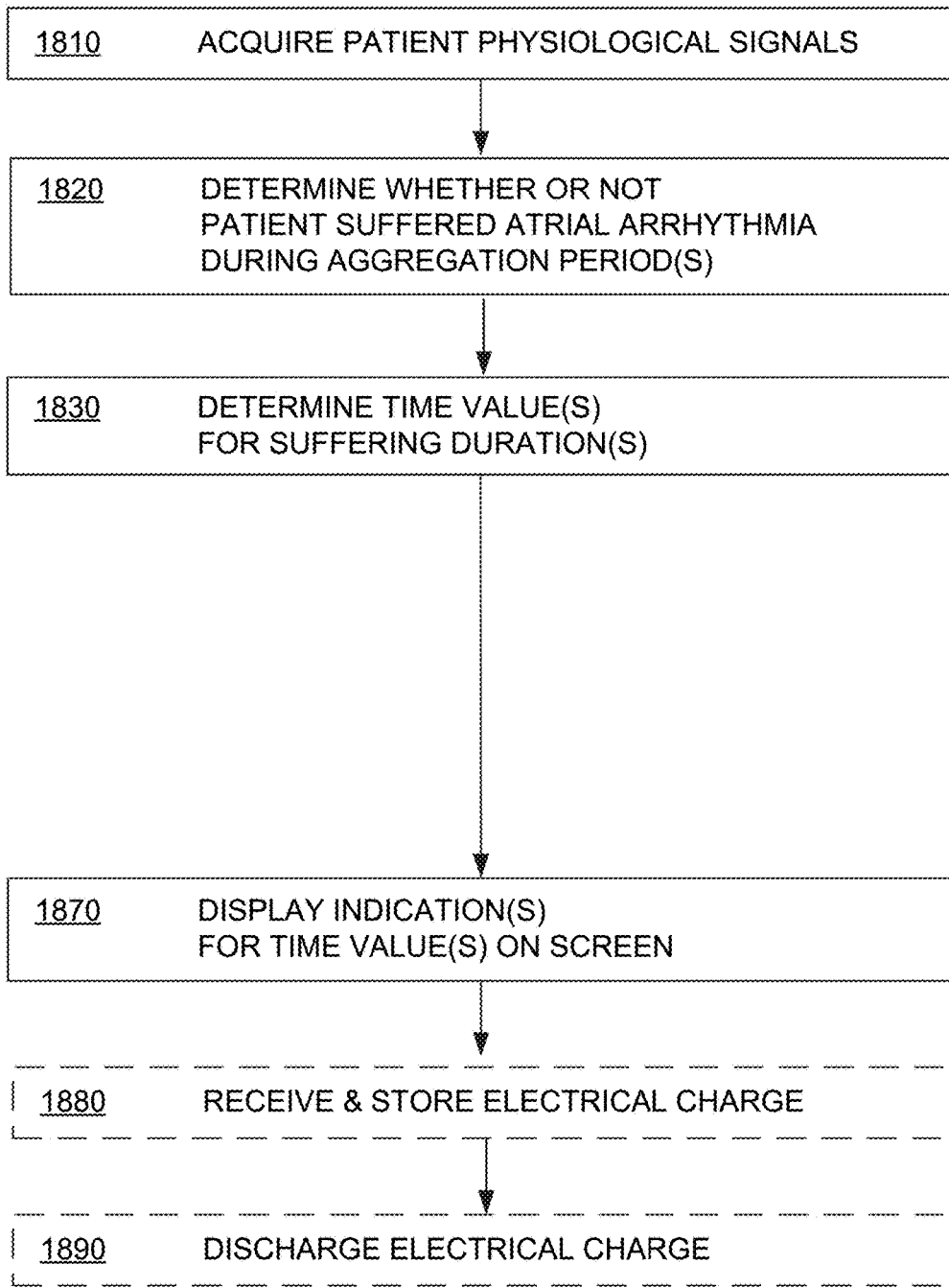
FIG. 18 is a flowchart for illustrating methods according to embodiments.

FIG. 18 shows a flowchart 1800 for describing methods according to embodiments. According to an operation 1810, patient physiological signals may be acquired by the one or more sensors of a WCD system, while the patient is wearing its support structure.

According to another operation 1820, it may be determined, from the physiological signals (e.g. the ECG data), whether or not the patient suffered an atrial arrhythmia during one or more aggregation periods. If so, then one or more respective time values of respective one or more suffering durations during which the patient so suffered may be determined.

According to another operation 1870, one or more respective indications may be displayed, for the one or more determined time values of the suffering durations. Other optional operations 1880 and 1890 can be as the previously described operations 680 and 690, respectively.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The description of this disclosure, which may be referenced elsewhere as "3332", is meant to be illustrative and not limiting on the scope of the following claims.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item. As used herein, the term "exemplary" is not intended to imply a superlative example. Rather, "exemplary" generally refers to an embodiment that is one of many possible embodiments.

What is claimed is:

1. A wearable cardioverter defibrillator (WCD) system, comprising:
    a support structure configured to be worn by a patient;
    a power source;
    an energy storage module configured to be coupled to the support structure, to receive an electric charge from the power source, and to store the received electric charge;
    a discharge circuit coupled to the energy storage module, the discharge circuit controllable to discharge an electric charge stored in the energy storage module while the support structure is worn by the patient;
    one or more sensors configured to acquire patient physiological signals during a time interval, the patient physiological signals including electrocardiogram (ECG) data of the patient;
    a processor configured to select a plurality of aggregation periods within the time interval and, for each aggregation period, to: a) identify one or more QRS complexes of the ECG data within the aggregation period, b) identify a representative width value for the identified one or more QRS complexes, and c) determine a representative heart rate value for the aggregation period;
    a memory configured to store, for at least some of the aggregation periods during the time interval, the rendered representative width values in association with the determined representative heart rate values; and
    wherein the processor is further configured to analyze a plurality of stored QRS width values in relation to their respective stored heart rate values and to determine a treatment to be provided to the patient based, at least in part, on that analysis.

2. The WCD system of claim 1, in which the time interval is one day or longer than one day.

3. The WCD system of claim 1, in which the time interval is one month or longer than one month.

4. The WCD system of claim 1, in which the aggregation period is 5 sec.

5. The WCD system of claim 1, in which the identified representative width value is a value of an average width of the identified QRS complexes within the aggregation period.

6. The WCD system of claim 1, in which the identified representative width value is a value of a width of one of the identified QRS complexes within the aggregation period.

7. The WCD system of claim 1, in which the representative heart rate value is determined as a statistic of determined heart rate values within the aggregation period.

8. The WCD system of claim 1, further comprising a communication interface which is configured to output the plurality of stored width values in relation to their respective stored heart rate values while the patient is wearing the support structure, and has been so wearing continuously since the patient physiological signals were acquired.

9. The WCD system of claim 1, further comprising a remote user interface that is configured to plot the plurality of stored width values in relation to their associated stored heart rate values.

10. The WCD system of claim 9, in which the remote user interface comprises a screen and is configured to be coupled to the support structure, and
    the screen is configured to display the plot while the patient is wearing the support structure.

11. The WCD system of claim 9, in which different versions of the plot are thus displayed at different times, and
    the memory is configured to store data files that encode the different versions of the plot.

12. The WCD system of claim 11, in which time stamps are further stored in the memory in association with the respective data files.

13. The WCD system of claim 11, in which an additional data file becomes thus stored after the passage of a preset aggregation time.

14. The WCD system of claim 11, in which an additional data file becomes thus stored after a preset number of representative heart rate values have been determined.

15. The WCD system of claim 11, further comprising:
    an input device; and in which
    an additional data file becomes thus stored responsive to receiving a user input from the input device.

16. A non-transitory computer-readable storage medium storing one or more programs which, when executed by at least one processor of a wearable cardioverter defibrillator (WCD) system, the WCD system also including: a support structure, a power source, an energy storage module coupled to the support structure, a discharge circuit, one or more sensors, and a memory, these one or more programs result in operations comprising:
    acquiring, by the one or more sensors, during a time interval, patient physiological signals that include electrocardiogram (ECG) data of the patient while the patient is wearing the support structure;
    selecting a plurality of aggregation periods within the time interval and, for each aggregation period in the plurality:
    a) identifying one or more QRS complexes of the ECG data within the aggregation period;
    b) identifying a representative width value for the identified one or more QRS complexes; and
    c) determining a representative heart rate value for the aggregation period;
    storing, for at least some of the aggregation periods, the identified representative width values in association with the determined representative heart rate values;
    determining whether an electric charge should be discharged based, at least in part, on an analysis of the stored width values in relation to their associated stored heart rate values;
    receiving, in the energy storage module, the electric charge from the power source, and storing the received electric charge; and
    discharging, by the discharge circuit, the electric charge stored in the energy storage module while the support structure is worn by the patient and when the analysis of the stored width values in relation to their associated stored heart rate values indicates that a defibrillation shock is necessary.

17. The medium of claim 16, in which the time interval is one day or longer than one day.

18. The medium of claim 16, in which the time interval is one month or longer than one month.

19. The medium of claim 16, in which the aggregation period is approximately 5 sec.

20. The medium of claim 16, in which the representative width value is a value of an average width of the identified QRS complexes within the aggregation period.

21. The medium of claim 16, in which the representative width value is a value of a width of one of the identified QRS complexes within the aggregation period.

22. The medium of claim 16, in which the representative heart rate value is determined as a statistic of determined heart rate values within the aggregation period.

23. The medium of claim 16, in which different versions of the stored width values in relation to their associated stored heart rate values are stored at different times, and the operations further comprise:
   storing, in the memory, data files that encode the different versions.

24. The medium of claim 23, in which time stamps are further stored in the memory in association with the respective data files.

25. The medium of claim 23, in which an additional data file becomes thus stored after the passage of a preset aggregation time.

26. The medium of claim 23, in which an additional data file becomes thus stored after a preset number of representative heart rate values have been determined.

27. The medium of claim 23, in which the WCD system further includes an input device, and
   an additional data file becomes thus stored responsive to a user input being received from the input device.

28. A method for using a wearable cardioverter defibrillator (WCD) system, the WCD system including: a support structure, a power source, an energy storage module coupled to the support structure, a discharge circuit, one or more sensors, a processor, and a memory, the method comprising:
   acquiring, by the one or more sensors, during a time interval patient physiological signals that include electrocardiogram (ECG) data of the patient while the patient is wearing the support structure;
   selecting a plurality of aggregation periods within the time interval and, for each aggregation period in the plurality:
   (a) identifying one or more QRS complexes of the ECG data within the aggregation period;
   (b) determining a representative width value for the identified one or more QRS complexes; and
   (c) determining a representative heart rate value for the aggregation period;
   storing, for at least some of the aggregation periods, the identified representative width values in association with the determined representative heart rate values;
   determining a treatment for the patient based on the stored width values in relation to their associated stored heart rate values;
   receiving, in the energy storage module an electric charge from the power source, and storing the received electric charge; and
   discharging, by the discharge circuit, the electric charge stored in the energy storage module while the support structure is worn by the patient and based on the determined treatment.

29. In combination, a wearable cardioverter defibrillator (WCD) system and a remote computer, the WCD system comprising:
   a support structure configured to be worn by a patient;
   a power source;
   an energy storage module configured to be coupled to the support structure, to receive an electric charge from the power source, and to store the received electric charge;
   a discharge circuit coupled to the energy storage module, the discharge circuit controllable to discharge an electric charge stored in the energy storage module while the support structure is worn by the patient;
   one or more sensors configured to acquire patient physiological signals during a time interval, the patient physiological signals including electrocardiogram (ECG) data of the patient;
   a local processor configured to perform the following local operations:
   select a plurality of aggregation periods within the time interval and,
   for each aggregation period, to: a) identify one or more QRS complexes of the ECG data within the aggregation period, b) determine a representative width value for the identified one or more QRS complexes, and c) determine a representative heart rate value for the aggregation period;
   a local memory configured to store data resulting from outcomes of the local operations;
   a local communication module configured to transmit data stored in the local memory via a communications link,
   while the remote computer comprises:
   a remote communication module configured to receive from the communications link the transmitted data; and
   a remote screen configured to display a plot of the stored width values versus their associated stored heart rate values.

30. In combination, a wearable cardioverter defibrillator (WCD) system and a remote computer, the WCD system comprising:
   a support structure configured to be worn by a patient;
   a power source;
   an energy storage module configured to be coupled to the support structure, to receive an electric charge from the power source, and to store the received electric charge;
   a discharge circuit coupled to the energy storage module, the discharge circuit controllable to discharge an electric charge stored in the energy storage module while the support structure is worn by the patient;
   one or more sensors configured to acquire patient physiological signals during a time interval, the patient physiological signals including electrocardiogram (ECG) data of the patient;
   a local processor configured to perform at least one of the following local operations:
   select a plurality of aggregation periods within the time interval, and
   for each aggregation period, to: a) identify one or more QRS complexes of the ECG data within the aggregation period, b) render a representative width value for the identified one or more QRS complexes, and c) determine a representative heart rate value for the aggregation period;
   a local memory configured to store data resulting from outcomes of the local operations;
   a local communication module configured to transmit data stored in the local memory via a communications link,
   while the remote computer comprises:
   a remote communication module configured to receive from the communications link the transmitted data;
   a remote memory configured to store the transmitted data;

a remote processor configured to perform whichever of the following remote operations that was not performed by the local processor:

select a plurality of aggregation periods within the time interval, and for each aggregation period, to: a) identify one or more QRS complexes of the ECG data within the aggregation period, b) render a representative width value for the identified one or more QRS complexes, and c) determine a representative heart rate value; and a remote screen configured to display a plot of the stored width values versus their associated stored heart rate values.

* * * * *